US010667925B2

(12) United States Patent
Emerick et al.

(10) Patent No.: US 10,667,925 B2
(45) Date of Patent: Jun. 2, 2020

(54) ADJUSTABLE INTERBODY FUSION DEVICE AND METHOD OF USE

(71) Applicant: BioSpine, LLC, Columbia City, IN (US)

(72) Inventors: Brian G. Emerick, Columbia City, IN (US); Daniel Refai, Atlanta, GA (US); Ross R. Nichols, North Webster, IN (US)

(73) Assignee: BioSpine, LLC, Columbia City, IN (US)

( * ) Notice: Subject to any disclaimer, the term of this patent is extended or adjusted under 35 U.S.C. 154(b) by 0 days.

(21) Appl. No.: 15/985,301

(22) Filed: May 21, 2018

(65) Prior Publication Data
US 2018/0263786 A1 Sep. 20, 2018

Related U.S. Application Data

(63) Continuation of application No. 14/763,311, filed as application No. PCT/US2014/012848 on Jan. 24, 2014, now Pat. No. 9,974,664.
(Continued)

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4611* (2013.01); *A61F 2/4603* (2013.01);
(Continued)

(58) Field of Classification Search
CPC .......... A61F 2/44; A61F 2/442; A61F 2/4425; A61F 2/4455; A61F 2/446; A61F 2/4465; A61F 2/447
(Continued)

(56) References Cited

U.S. PATENT DOCUMENTS 4,759,769 A 7/1988 Hedman
6,685,742 B1 2/2004 Jackson
(Continued)

FOREIGN PATENT DOCUMENTS

EP 2226039 9/2010
WO 2010033445 3/2010
(Continued)

OTHER PUBLICATIONS

International Search Report and Written Opinion of the International Searching Authority for PCT/US2014/012848, dated Apr. 18, 2015, 12 pages.
(Continued)

*Primary Examiner* — Julianna N Harvey
*Assistant Examiner* — Christina Negrellirodriguez
(74) *Attorney, Agent, or Firm* — Heslin Rothenberg Farley & Mesiti P.C.; Kristian E. Ziegler

(57) ABSTRACT

Interbody fusion devices, interbody fusion device systems, insertion tools, methods for assembling an interbody fusion device, and methods a method for inserting a medical device between two vertebral bodies are disclosed. The interbody fusion device includes a body member with a pivot cylinder, a superior member with a pivot channel that is configured to engage the pivot cylinder, and a movement mechanism for moving the superior member relative to the body member. The interbody fusion device systems may include an interbody fusion device and an insertion tool. Also disclosed is a method of assembling an interbody fusion device. In addition, a method for inserting a medical device between two vertebral bodies in a spine is disclosed.

27 Claims, 18 Drawing Sheets

Related U.S. Application Data

(60) Provisional application No. 61/756,048, filed on Jan. 24, 2013.

(52) U.S. Cl.
CPC .......... *A61F 2002/3054* (2013.01); *A61F 2002/3082* (2013.01); *A61F 2002/30471* (2013.01); *A61F 2002/30476* (2013.01); *A61F 2002/30525* (2013.01); *A61F 2002/30579* (2013.01); *A61F 2002/30593* (2013.01); *A61F 2002/30601* (2013.01); *A61F 2002/30772* (2013.01); *A61F 2002/30797* (2013.01); *A61F 2002/30828* (2013.01); *A61F 2002/30904* (2013.01); *A61F 2002/4627* (2013.01); *Y10T 29/25* (2015.01)

(58) Field of Classification Search
USPC .............. 606/246–249; 623/17.11–17.16
See application file for complete search history.

(56) References Cited

U.S. PATENT DOCUMENTS

| | | | |
|---|---|---|---|
| 8,011,551 | B2 | 9/2011 | Marczyk |
| 8,070,813 | B2 | 12/2011 | Grotz |
| 8,075,600 | B2 | 12/2011 | Schläpfer |
| 8,303,663 | B2 * | 11/2012 | Jimenez ............ A61B 17/7065 623/17.16 |
| 2002/0173817 | A1 | 11/2002 | Kletschka |
| 2009/0299478 | A1 | 12/2009 | Carls |
| 2010/0168861 | A1 | 7/2010 | Yundt |
| 2010/0274299 | A1 | 10/2010 | Lawson |
| 2011/0106172 | A1 | 5/2011 | Wallenstein |
| 2011/0245927 | A1 | 10/2011 | Farris |
| 2012/0310350 | A1 | 12/2012 | Farris |

FOREIGN PATENT DOCUMENTS

| | | |
|---|---|---|
| WO | 2010120782 | 10/2010 |
| WO | 2011011609 | 1/2011 |
| WO | 2013155418 | 10/2013 |
| WO | 2013158294 | 10/2013 |
| WO | 2014116891 | 7/2014 |

OTHER PUBLICATIONS

Preliminary Report on Patentability for PCT/US2014/012848, dated Aug. 6, 2015, 11 pages.
Response to Communication Pursuant to Rules 161(1) and 162 EPC for European Application No. 14742780.1, dated Mar. 11, 2016, 12 pages.
Extended European Search Report for European Application No. 14742780.1, dated Dec. 20, 2016, 6 pages.
Response to Communication Pursuant to Rules 70(2) and 70a(2) for European Application No. 14742780.1, dated Jul. 19, 2017, 14 pages.

* cited by examiner

ADJUSTABLE INTERBODY FUSION DEVICE AND METHOD OF USE

CROSS-REFERENCE TO RELATED APPLICATIONS

This application is a continuation of U.S. application Ser. No. 14/763,311 filed Jul. 24, 2015, which will issues as U.S. Pat. No. 9,974,664 on May 22, 2018, which is a U.S. National Stage Filing under 35 U.S.C. § 371 from International Application No. PCT/US2014/012848 filed on Jan. 24, 2014, and published as WO 2014/116891 on Jul. 31, 2014, which claims priority benefit under 35 U.S.C. § 119(e) of U.S. provisional application No. 61/756,048 filed Jan. 24, 2013, which applications are incorporated herein by reference in their entireties.

TECHNICAL FIELD

The present invention relates generally to general surgery, orthopaedic and neurosurgical implants used for insertion within a space between hard tissue structures, and more specifically, but not exclusively, concerns devices implanted between bones to replace resected, fractured or diseased structures and to maintain or reestablish proper spacing between two bones.

BACKGROUND OF THE INVENTION

Damage or disease that affects the integral structure of a bone or other structures, may lead to neurologic impairment or loss of structural support integrity with possible permanent damage to the surrounding soft tissue and adjacent neurologic, vascular and systemic structures. Maintaining or reestablishing anatomic spacing within a bone structure or other structural tissue is critical to ensuring continued functionality and mobility of the patient and avoidance of long-term serious neurological, vascular or other systemic impairments. Please note that the terms "implant" and "device" may be used interchangeably and have the same meaning herein.

SUMMARY OF THE INVENTION

Advancement of the state of interbody fusion devices and implants and the surgical management relating to the clinical presentation of damaged tissue structures within the body is believed desirable. Example embodiments of the invention that satisfies the need for improvements to an expandable interbody fusion device used to treat patients suffering from either diseased or damaged disc or other tissue structures includes a superior member coupled to a body member.

The present invention provides in one aspect, an interbody fusion device having a body member including a pivot cylinder, a superior member including a pivot channel, and a movement mechanism for moving the superior member relative to the body member. The pivot cylinder being configured to engage the pivot channel.

The present invention provides in another aspect, an interbody fusion device system. The system including an interbody fusion device and an insertion tool. The interbody fusion device may include a base member with a pivot cylinder, a top member with a hinge channel, and an expansion mechanism for moving the top member relative to the base member. The pivot cylinder may be configured to engage the hinge channel. The insertion tool may include a handle, an insertion end, at least one tube extending away from the handle and connecting the handle and the insertion end. The tool may also include a first knob configured to couple to the handle. The tool may further include an actuation bar moveable between a first and second position to enable the first knob to engage an adjustment mechanism in the first position and a securement mechanism in the second position.

The present invention also provides in another aspect, a method for assembling an interbody fusion device, including obtaining a bottom member, an expansion mechanism, and a top member. The method may also include inserting the expansion mechanism into the bottom member and securing a first portion of the expansion mechanism in the bottom member. In addition, the method may include coupling the top member to the bottom member. The method may further include aligning the top member with the bottom member and a second portion of the expansion mechanism.

The present invention provides in yet another aspect, a method for inserting a medical device between two vertebral bodies in a spine. The method may include obtaining a medical device. The medical device may include a base member, a top member configured to be coupled to the base member, and a movement mechanism engaging the top member and the base member. The method may also include inserting and coupling a tool into at least two openings within the medical device. The method may further include slidingly inserting the medical device into a space between two vertebral bodies. The method may also include rotating a knob of the tool to move a first end of the top member in a vertical direction relative to the base member.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which:

DETAILED DESCRIPTION

Generally stated, disclosed herein is an interbody fusion device or interbody device that typically includes a top member, a base member, and at least one expansion mechanism. Further, the interbody fusion device may include an extendable/retractable member or expansion assembly and an expansion tool for expansion and contraction of the interbody device. The retractable member extending in a vertical direction. As used herein, the terms "interbody fusion device," "medical device," "device," "interbody device" and "implant" may be used interchangeable as they essentially describe the same type of device. Further, the corresponding expansion tool may also be referred to as "tool" or "instrument" and these terms may be used interchangeably. Finally, described herein is a surgical method for using the interbody fusion device to maintain a space between two vertebral bodies within a patient suffering from a diseased or damaged disc or spinal column.

As depicted in FIGS. 1-8, the general arrangement of an adjustable interbody fusion device 100, in accordance with an aspect of the present invention, includes a base member 110, a top member 130, and an expansion mechanism 140. In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

Figure 1:
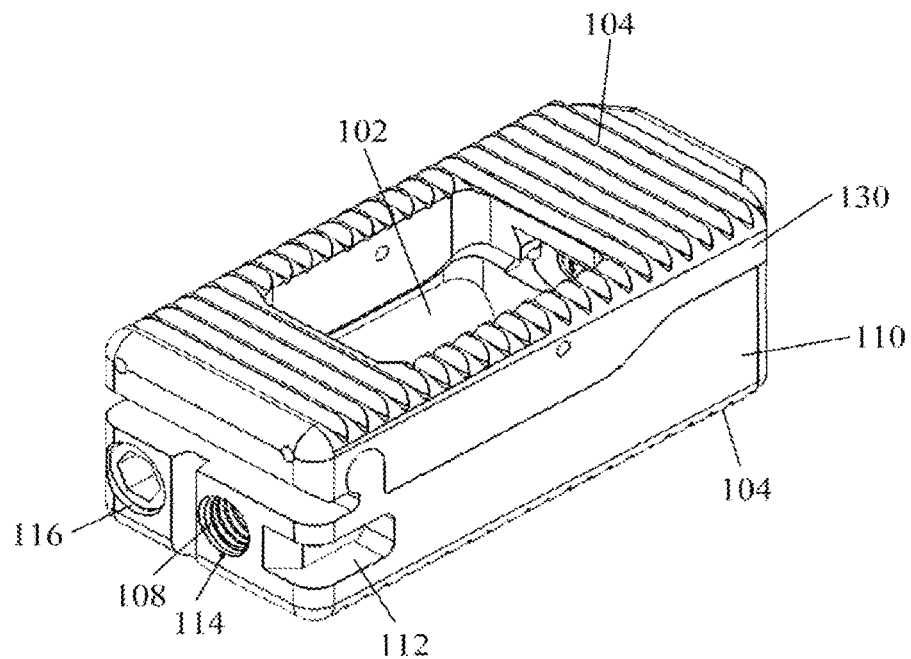
FIG. 1 is a posterior perspective view of one embodiment of an expandable interbody fusion device, in accordance with an aspect of the present invention.
Figure 2:
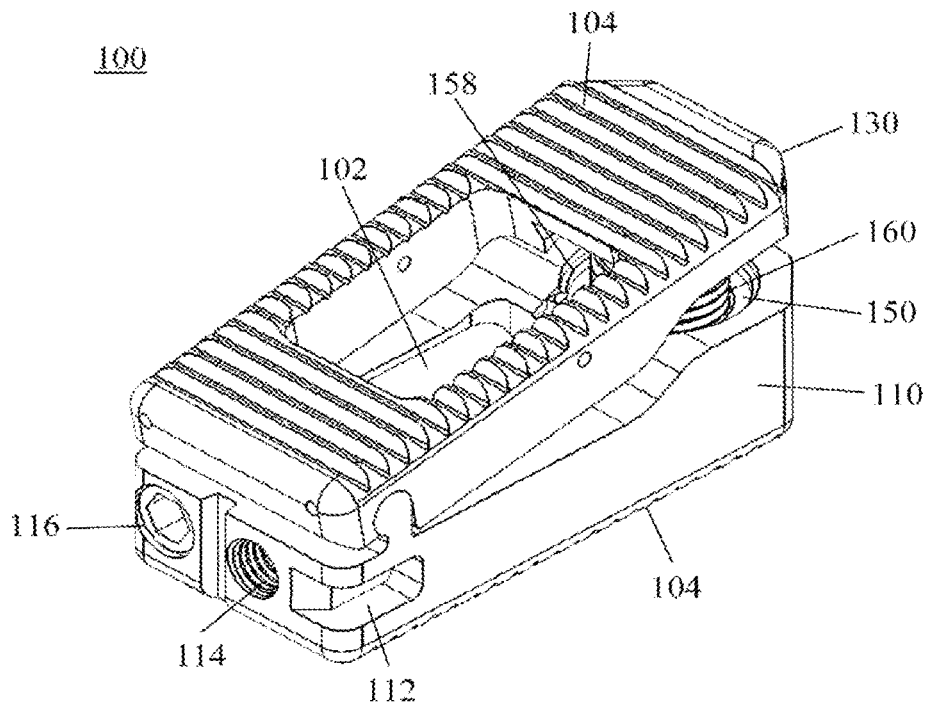
FIG. 2 is an isometric view of the expandable interbody fusion device of FIG. 1 with the moveable member extended, in accordance with an aspect of the present invention.
Figure 3:
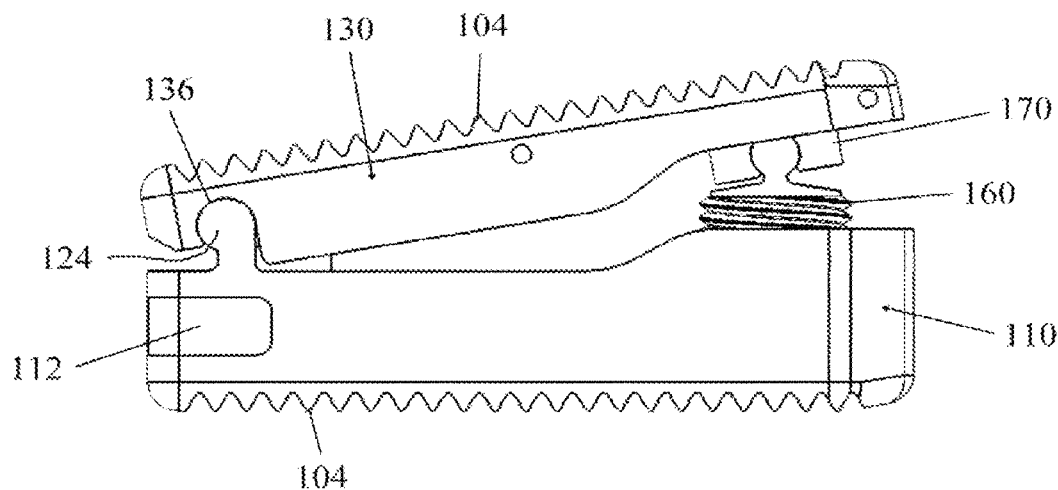
FIG. 3 is a side view of the expandable interbody fusion device of FIG. 1 with a moveable member extended, in accordance with an aspect of the present invention.

It is shown in FIGS. 1-3, the example of the adjustable interbody fusion device 100. The device 100 as seen in FIG. 1 may have, for example, a generally rectangular geometry with various configured long sides to facilitate insertion and bone coverage. Although it would be understood by one skilled in the art that other outside configurations can be used. The implant 100 may likely include at least one moveable top or superior member 130 and a base, body, or bottom member 110. The top member 130 may be detachably coupled to the base member 110.

As seen in FIGS. 1 and 2, base member 110 may have at least one through hole or central opening 102 for insertion of bone graft material disposed on the inferior and superior bone contacting surfaces 104. The opening 102 typically extends through both bone contacting surfaces 104 of the base and top members 110, 130 and into the inner cavity of the assembled device 100. The size and configuration of the opening 102 allow the surgeon to place bone graft material inside the implant 100 to achieve a continuous fusion between the inferior and superior vertebral bodies.

As shown in FIG. 1, the superior and inferior bone contacting surfaces 104 may be generally parallel to each other. However, the expansion mechanism or movement mechanism 140 (these names may be used interchangeably), (see FIG. 8), will allow the user to angle one end of the bone contacting surface 104 of the top member 130 relative to the bone contacting surface 104 of the base member 110 as seen in FIGS. 2 and 3, wherein the far end is fully expanded and the near end remains retracted. FIGS. 1-4 show the bone contacting surfaces 104 to have teeth-like or tine structures projecting away from the superior and inferior surfaces. One skilled in the art would recognize that other surface treatments may be applied to the bone contacting surfaces 104 to enhance fixation with the opposing bone surface. Although not shown, it is understood by one skilled in the art that modular bone contacting surfaces, caps or plates may be used to provide for varying types of bone contacting surfaces and structures, including, but not limited to sharp tines, porous coatings, biomaterial or ingrowth surfaces, and ridge structures. It is also understood that the bone contacting surfaces 104 may be coated with nano-surfacing, bioactive or bone/tissue ingrowth coatings.

Figure 4:
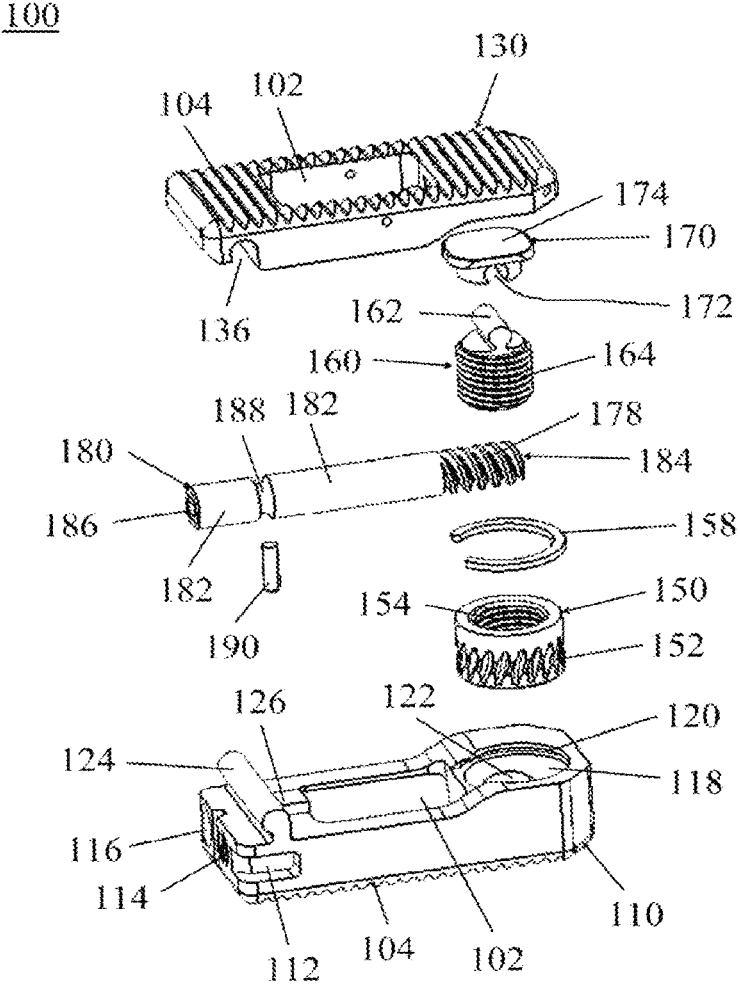
FIG. 4 is an exploded view of the expandable interbody fusion device of FIG. 1, in accordance with an aspect of the present invention.
Figure 5:
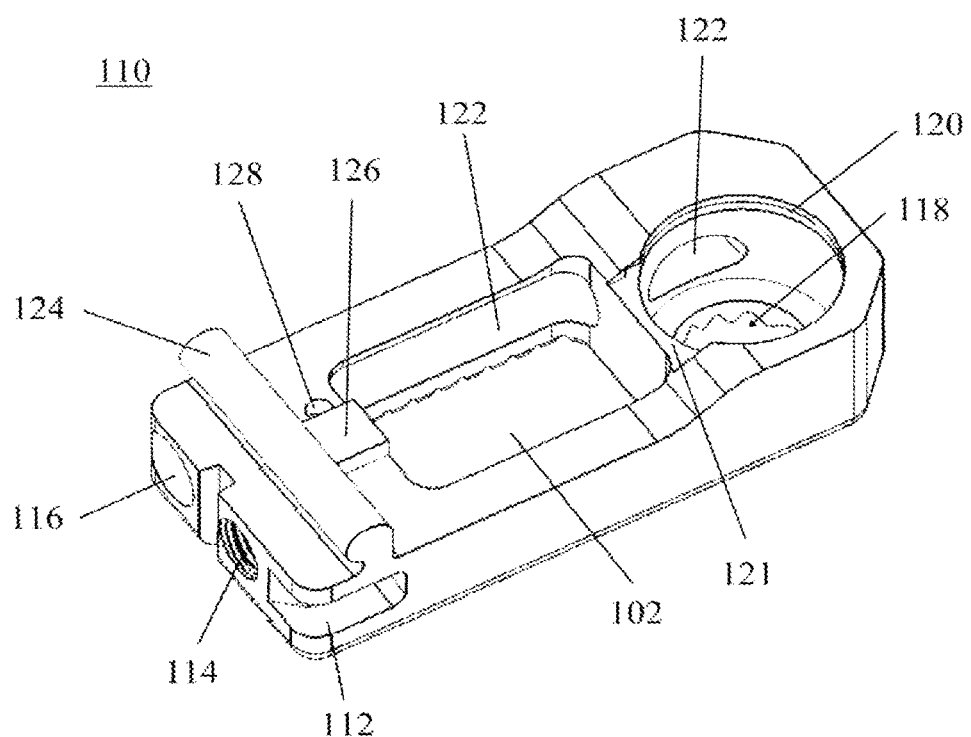
FIG. 5 is a superior perspective view of the expandable interbody fusion device of FIG. 1, showing only the base or bottom member, in accordance with an aspect of the present invention.

As seen in FIGS. 4 and 5, the base member 110 may also include a tool alignment channel 112 extending along a side of the base member 110 from the posterior end, a tool attachment opening 114 on the posterior end of the base member 110, and an adjustment opening 116 on the posterior end of the base member 110 and which may be opposite the tool alignment channel 112, as seen in FIGS. 1 and 2. The base member 110 may also include a hole or lumen 118 near the proximal end of the base member 110 to house an expansion mechanism 140 (see FIG. 8), which will be discussed in greater detail below. The hole 118 may have a smooth vertical wall to facilitate insertion and unrestricted rotation of a cylindrical gear 150 of the expansion mechanism 140 (see FIG. 8). The hole 118 of the base member 110 may also include an internal circumferential shoulder 120 and a notch 121. In addition, the base member 110 may include a channel 122 extending from the adjustment opening 116 interiorly along a lateral side of the base member 110 to engage the hole 118. The base member 110 may also include a pivot cylinder 124, an alignment protrusion 126, and an opening 128.

Figure 6:
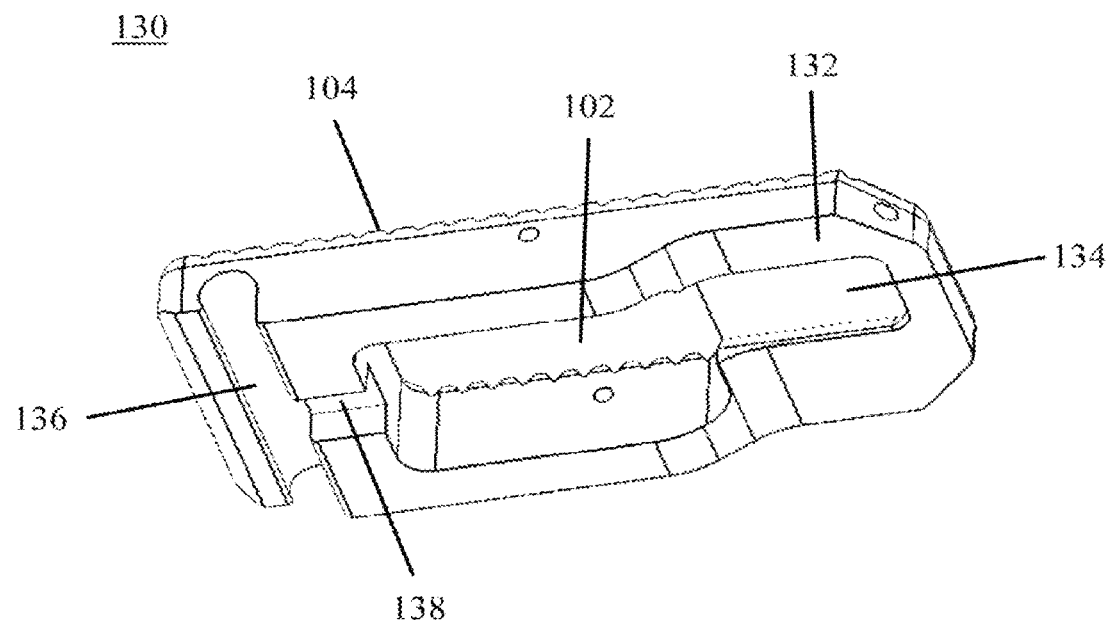
FIG. 6 is an inferior perspective view of the expandable interbody fusion device of FIG. 1, showing only the top or superior member, in accordance with an aspect of the present invention.

As seen in FIGS. 4 and 6, the top or superior member 130 also includes an undersurface 132 with a relief area 134 that is adjacent to the central opening 102. The central opening 102 may be configured to permit the surgeon to insert bone graft material into the inner cavity of the implant 100 prior to implantation. The relief area 134 may be substantially planar and the relief area 134 may be aligned with the hole 118 in the base member 110. The relief area 134 is relatively rectangular with the long axis of the rectangle extending along the longitudinal axis of the top member 130. The relief area 134 is configured to mate with a correspondingly shaped load head 170 of the expansion mechanism 140 (see FIG. 8). The top member 130 may also include a hinge channel or pivot channel 136 for mating with the pivot cylinder 124 of the base member 110 to enable the implant 100 to extend on the proximal end while remaining closed on the distal end. The pivot cylinder 124 and hinge channel 136 allow the top member 130 to pivot or rotate around the outer diameter of the pivot cylinder 124 of the base member 110 when expansion assembly 142 (see FIG. 8) is extended or retracted causing the top member 130 to tilt or slant relative to the base member 110. In addition, the top member 130 may include an opening 138 for mating with the alignment protrusion 126 of the base member 110.

Figure 8:
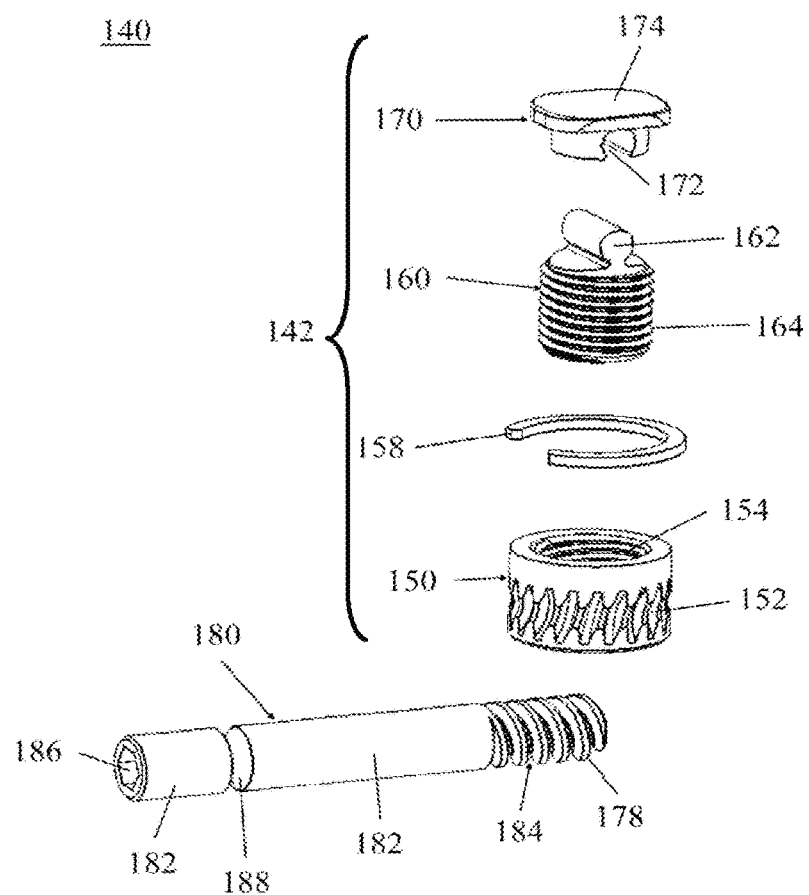
FIG. 8 is an exploded view of the expansion mechanism of the expandable interbody fusion device of FIG. 1, in accordance with an aspect of the present invention.

Referring now to FIG. 4 with continued reference to FIGS. 5 and 6, an exploded view of all of the components that comprise the implant 100 is shown. As shown in FIG. 8, the expansion mechanism 140 of the implant 100 includes an expansion assembly 142 and a drive rod 180. The expansion assembly 142 may include a cylindrical gear 150, a support means 158, a threaded rod 160, and a load head 170. The vertical cylinder or cylindrical gear 150 (these names may be used interchangeably) may nest or be suspended within the hole 118 of the base member 110. The cylindrical gear 150 may include external substantially vertical depressions or circumferential serial depressions 152 positioned on the outer surface of the gear 150 which extend around the entire circumference. For example purposes, the gear 150 may have a smooth surface, above and below the substantially vertical depressions 152. Positioning the circumferential serial depressions 152 around the central portion of the gear 150 may maximize strength and improve trackability when the cylindrical gear 150 engages the drive rod 180. The circumferential serial depressions 152 may also include uniquely oriented thread patterns. In addition, the gear 150 may include internal threads 154 on the interior surface of the gear 150.

Figure 7:
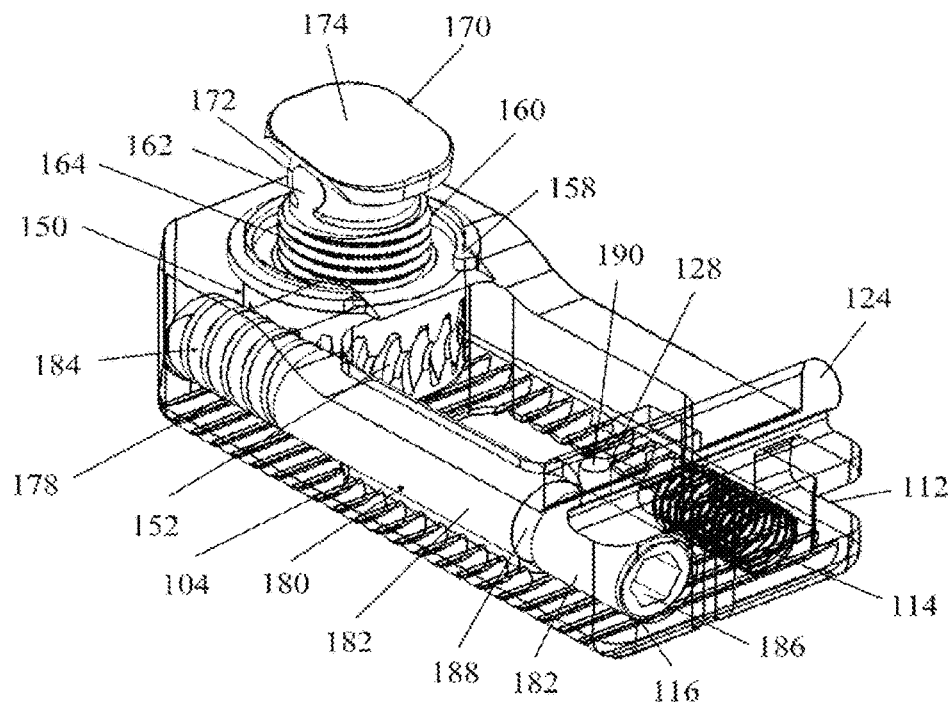
FIG. 7 is a posterior elevational view of the expandable interbody fusion device of FIG. 1 without the top member, showing the expansion assembly extended and tilted to accommodate the slanted top member, in accordance with an aspect of the present invention.

As shown in FIG. 7, the support means 158 may sit on the shoulder 120 (see FIG. 5) of the base member 110 and function to maintain the expansion assembly 142 (see FIG. 8) in a vertical orientation relative to the base member 110 and aligned with the hole 118. The support means 158 may also be used adjacent to the gear 150 and threaded rod 160 and may hold the gear 150 in the hole 118 (see FIG. 5). The support means may, for example, be in the form of a ring, snap ring, washer or other similar type of structure that will secure the expansion assembly 142 (see FIG. 8) to the base member 110. The shoulder 120 may also operate as a bearing surface against which the support means 158 contacts to facilitate the rotation of the expansion assembly 142 when actuated. As shown in FIG. 5, the notch 121 in the hole 118 of the base member 110 may enable the support means 158 to be inserted into the shoulder 120.

As shown in FIGS. 4, 7 and 8, the threaded rod 160 may include a pivot cylinder 162 located on the top or superior end of the threaded rod 160. The threaded rod 160 may also include external threads 164 extending along its length. The external threads 164 may be configured to match the internal threads 154 of the gear 150. The pivot cylinder 162 of the threaded rod 160 may be inserted into a distal channel 172 of the load head 170. These constructs allow the load head 170 to pivot, slide, or rotate around the outer diameter of the pivot cylinder 162 when the threaded rod 160 is extended causing the top member 130 to tilt or slant. A tilted or slanted load head 170 is shown in FIGS. 3 and 7. The load head 170 may also include a superior head surface 174. The superior head surface 174 may be shaped to match with the corresponding relief area 134 (see FIG. 6) on the undersurface 132 of the top member 130. The superior head surface 174 is configured to slide along the relief 134 of the undersurface 132, if necessary, to allow for the expansion assembly 142 to lengthen to create the angled relationship of the top member 130 relative to the base member 110. The relief 134 in the undersurface 132 and the correspondingly shaped load head 170 facilitates the angulation process and the load transfer between the top member 130 and the base member 110 while avoiding potential binding of the expansion assembly 142 during the expansion and retraction process.

The drive rod 180 of the expansion mechanism 140 (see FIG. 8) may be inserted into the adjustment opening 116 and sit in the channel 122 of the base member 110, as shown in FIGS. 4 and 7. The drive rod 180 may be comprised of a cylindrical shaft 182 with a worm gear 184 at one end of the cylindrical shaft 182. The cylindrical shaft 182 may also have an opening 186 at a second end of the cylindrical shaft 182 opposite the worm gear 184 for coupling with a tool 200. In addition, the cylindrical shaft 182 may include a channel 188 for mating with a pin 190 to secure the drive rod 180 in the base member 110 to enable adjustment of the top member 130 without the drive rod 180 backing out of the implant 100. The pin 190 may also prevent the drive rod 180 from backing out of the implant 100 after implantation into the patient's spine. By off-centering the adjustment opening 116 and the channel 122 from the longitudinal axis of the device 100, the worm gear 184 of the drive rod 180, which is inserted into the channel 122, intersects with the hole 118 of the base member 110. The worm gear 184 may be configured to engage with the gear 150 of the expansion assembly 142 which sits in the hole 118 of the base member 110. FIG. 7 shows the assembled implant 100 without the top member 130 with the drive rod 180 positioned and extending through the length of the base member 110.

Figure 12:
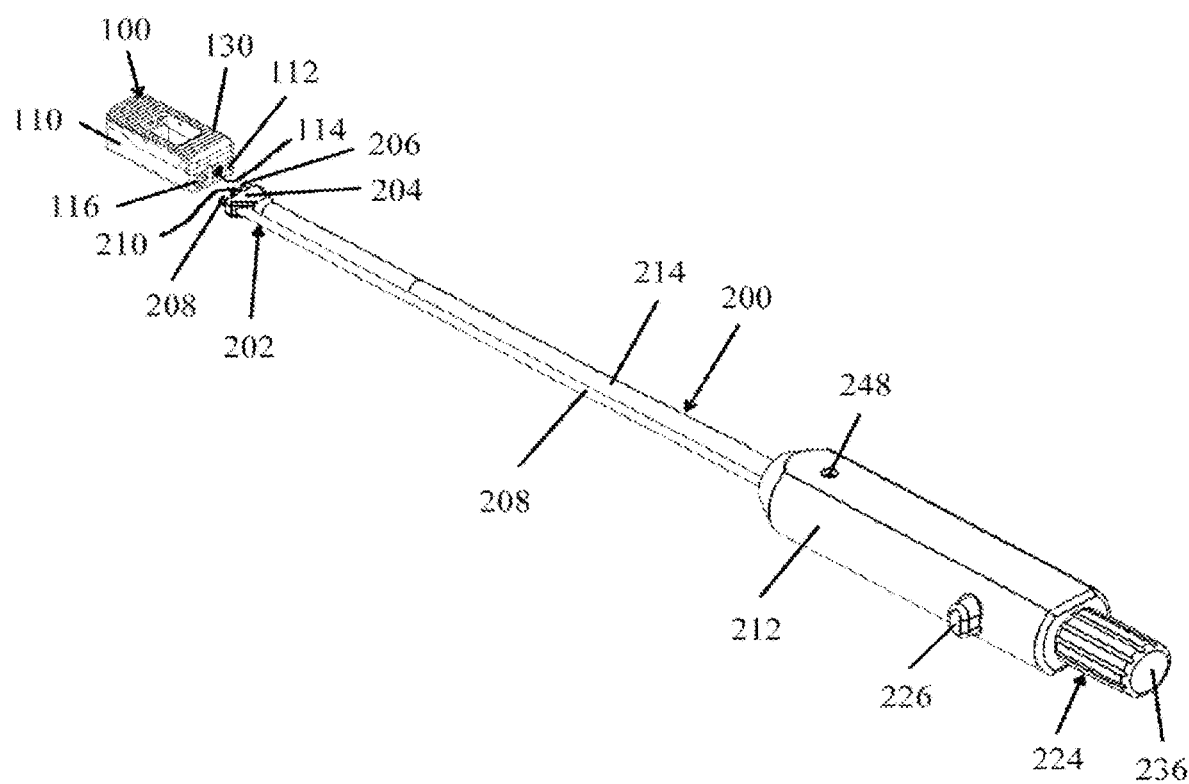
FIG. 12 is a perspective view of the expandable interbody fusion device of FIG. 1 and an expansion tool, in accordance with an aspect of the present invention.
Figure 13:
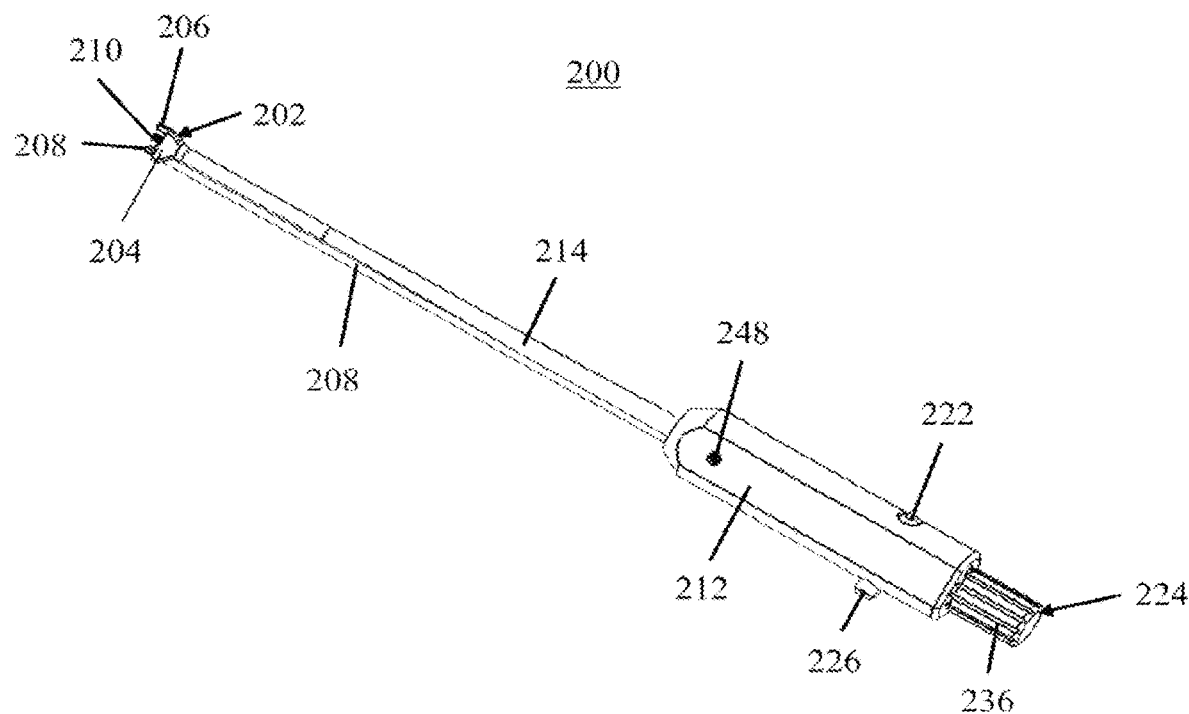
FIG. 13 is a top perspective view of the expansion tool of FIG. 12, in accordance with an aspect of the present invention.
Figure 14:
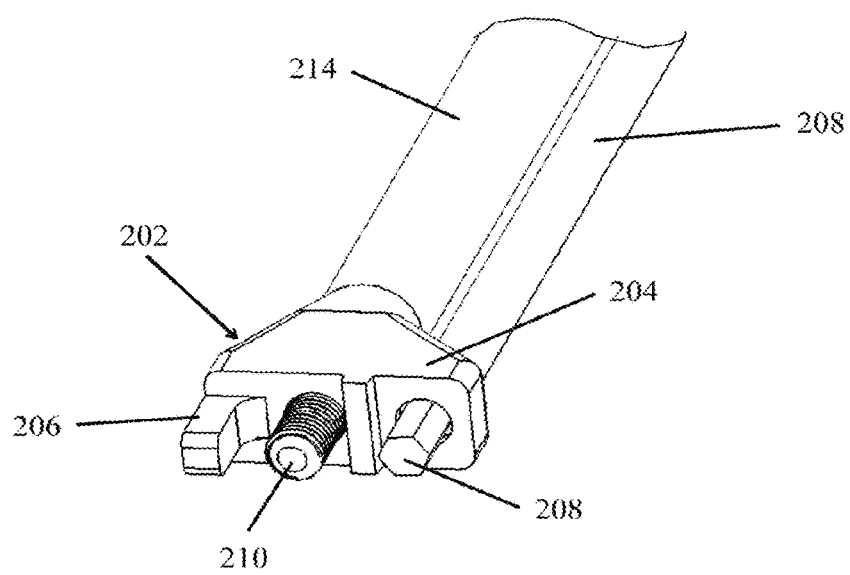
FIG. 14 is a truncated anterior view of the attachment end of the expansion tool of FIG. 12, in accordance with an aspect of the present invention.

When the implant 100 is inserted into a patient using tool 200, as shown in FIG. 12, the tool 200 engages the alignment channel 112, the attachment opening 114 and the adjustment opening 116, as described in greater detail below. Once the tool 200 is inserted into the patient between two vertebrae, the drive rod 180 with the gear 150 function to mirror the rotational movement exerted by the tool 200, described in greater detail below, and translate the movement to the gear 150. The expansion mechanism 140 functions to convert rotation movement of the gear 150 into linear or translational movement of the load head 170 positioned at the superior end of the threaded rod 160. Rotation of the gear 150 will result in a travel distance of the threaded rod 160 when the expansion mechanism 140 is actuated by the tool 200. As the gear 150 is coupled to the drive rod 180, the coupled gear 150 will turn as the drive rod 180 is rotated, thus avoiding the need for the tool 200 to pass through the entire length of the channel 122 to engage the gear 150 on the far end of the implant 100.

With continued reference to FIGS. 1-8, as the drive rod 180 is rotated by the tool 200, the teeth 178 of the worm gear 184 positioned on the end of the drive rod 180 are configured to mate with the substantially vertical depressions 152 of the gear 150. As described above, the expansion assembly 142 acts to convert rotational movement of the gear 150 into translational movement of the threaded rod 160. This is achieved by allowing free rotational movement of the gear 150 while restricting the rotation of the threaded rod 160. By restricting the rotation of the threaded rod 160, the rod translates in either an upward or downward direction relative to the gear 150 depending upon whether the threads (external and internal) 154, 164 are oriented in a right-handed or left-handed direction. As discussed above, when the threaded rod 160 moves, the load head 170 contacts the relief area 134 of the undersurface 130 of the top member 130 to either move it away from or towards the base member 110. In other words, the height of the implant 100 either increases or decreases or the bone contacting surface 104 will be angled relative to the base member 110 depending on the rotational direction of the tool 200.

Figure 9:
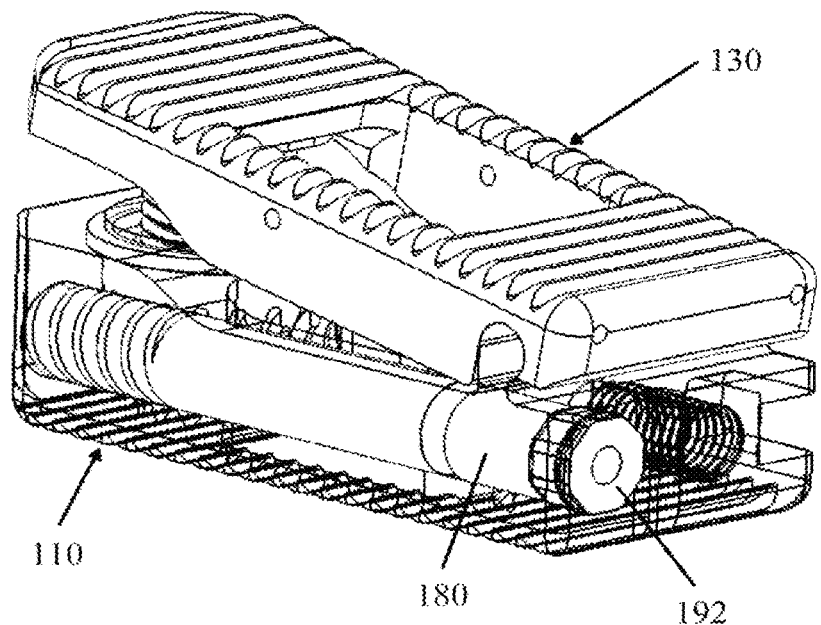
FIG. 9 is an isometric view of another expandable interbody fusion device with a transparent base member showing a drive rod and locking mechanism, in accordance with an aspect of the present invention.
Figure 10:
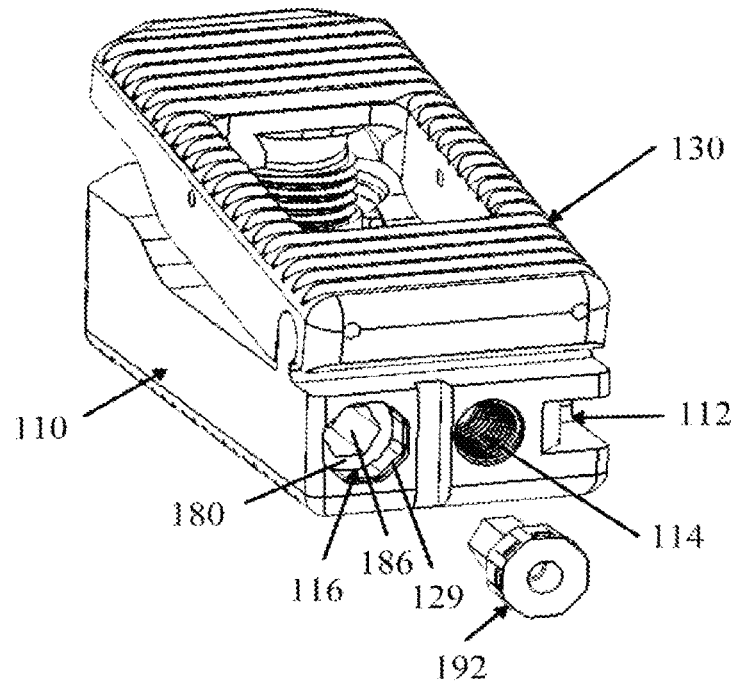
FIG. 10 is a partially exploded isometric view of the expandable interbody fusion device of FIG. 9 showing the locking mechanism being inserted into the interbody fusion device, in accordance with an aspect of the present invention.
Figure 11:
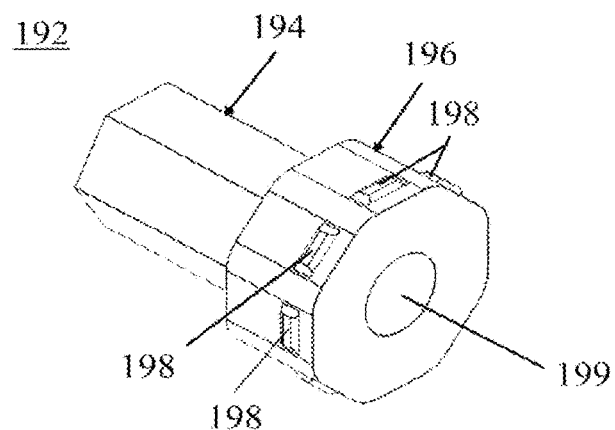
FIG. 11 is an isometric view of the locking mechanism of FIGS. 9 and 10, in accordance with an aspect of the present invention.

Referring now to FIGS. 9-11, an alternative embodiment adjustable interbody fusion device 100 including a locking mechanism 192 is shown. As shown in FIG. 11, the locking mechanism 192 may include a shaft 194 extending out from a head 196. The head 196 may include a plurality of protrusions 198 for engaging the lip 129 (see FIG. 10) in the adjustment opening 116 of the base member 110 to secure the locking mechanism 192 in the base member 110. The head 196 may also include an opening 199 for engaging the insertion tool 200 or a similar tool. The shaft 194 of the locking mechanism 192 may have a shape which corresponds to the shape of the tool opening 186 of the drive rod 180, for example, the shape may be a hexagon, square, or other multi-lobed configuration allowing the shaft 194 of the locking mechanism 192 to fit securely within the opening 186 of the drive rod 180. Similarly, the head 196 may have a shape which corresponds to the shape of the adjustment opening 116, for example, the shape may be a circle, hexagon, square, or other multi-lobed configuration allowing the locking mechanism 192 to securely fit within the adjustment opening 116 of the base member 110 to secure the locking mechanism 192 in the implant 100 to maintain a desired expansion or retraction. Other shapes for the shaft 194 and the head 196 of the locking mechanism 192 are also contemplated. The locking mechanism 192 may be, for example, made of a rigid material or a deformable material. If the locking mechanism 192 is made of a deformable material it may be made slightly larger than the opening 186 in the drive rod 180 and/or the adjustment opening 116 in the base member 110, such that once it is inserted the larger size locks the drive rod 180 in the desired position.

Referring now to FIGS. 12-19, a tool 200 for inserting the implant 100 into a patient is shown. The tool 200 and the implant 100 may form an interbody fusion device system, as shown in FIG. 12. The tool 200 is designed to engage the expansion mechanism 140 (see FIG. 8). The insertion end 202 of the tool 200 may be configured with a housing 204 including a protrusion or alignment protrusion 206 shaped to correspond to the alignment channel 112 in the base member 110. The insertion end 202 may also include an adjustment mechanism 208 and a securement mechanism 210 which protrude out of the distal end of the housing 204. The adjustment mechanism 208 may be configured, for example, to have a hex male head, square, or other multi-lobed configuration that will allow for the user to rotate the knob 224 of the tool 200 and cause the expansion mechanism 140 to rotate. Opposite the insertion end 202, the tool 200 has a handle 212 which may be connected to the housing 204 of the insertion end 202 by a tube 214. The tube 214 may be coupled to the housing 204 on the distal end and secured to the handle 212 at the proximal end by fasteners 248, for example, screws. The tube 214 may house the securement mechanism 210 which may extend from the handle 212 to the housing 204 inside the tube 214. In addition, the adjustment mechanism 208 may also extend between the housing 204 at the insertion end 202 and the handle 212, relatively parallel to and outside the tube 214.

As seen in FIGS. 15-18, the handle 212 of the tool 200 may also include a first opening 216 and a second opening 218 along the longitudinal axis of the handle 212. In addition, the handle 212 of tool 200 may include a third opening 220 extending perpendicular to and engaging the first and second openings 216, 218. A fourth opening 222 may also be in the handle 212 and may extend into the handle 212 from the proximal end of the handle 212 into the third opening 220 and may run parallel with the first and second openings 216, 218. The handle 212 may also include a knob 224 which may be inserted into both the first and second openings 216, 218 at a proximal end of the handle 212, an actuation bar 226 for insertion into the third opening 220, and a spring plunger 228 for insertion into the fourth opening 222. The knob 224 may include a head 236 with a shaft 238 extending out away from the inferior surface of the head 236. The shaft 238 of the knob 224 may also include a channel 240 for mating with the actuation bar 226 to secure the knob 224 in the inserted opening 216, 218.

Figure 15:
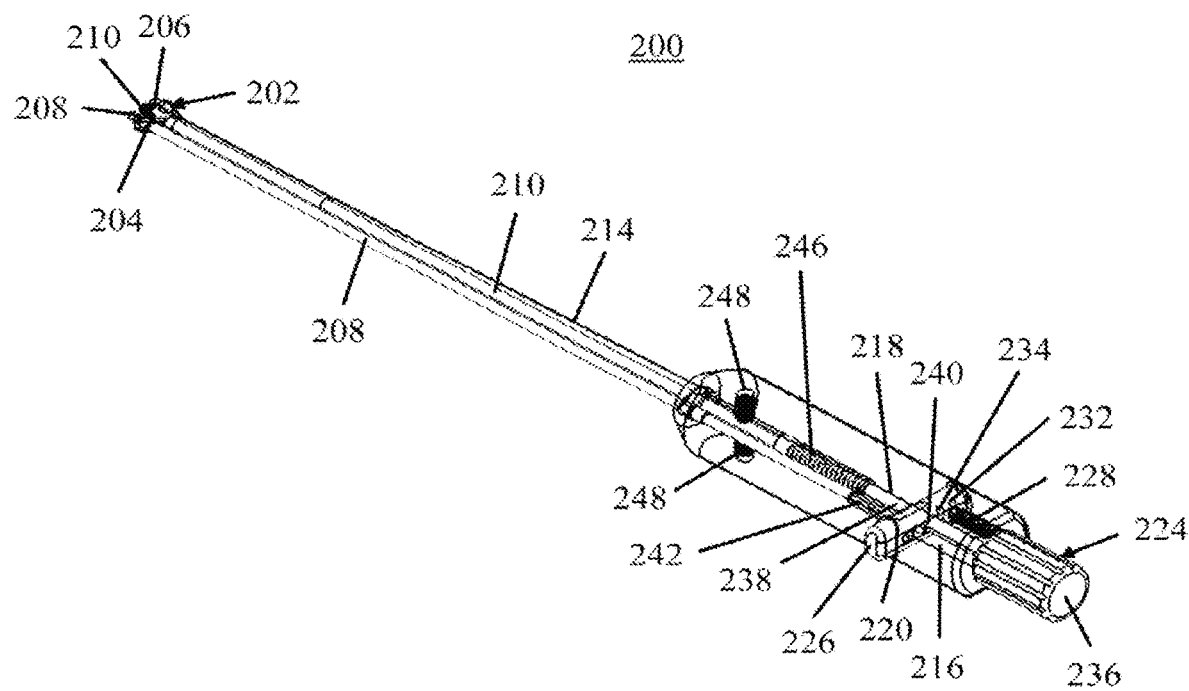
FIG. 15 is a perspective view of the expansion tool of FIG. 13 with a transparent outer housing and the knob in a first position, in accordance with an aspect of the present invention.
Figure 16:
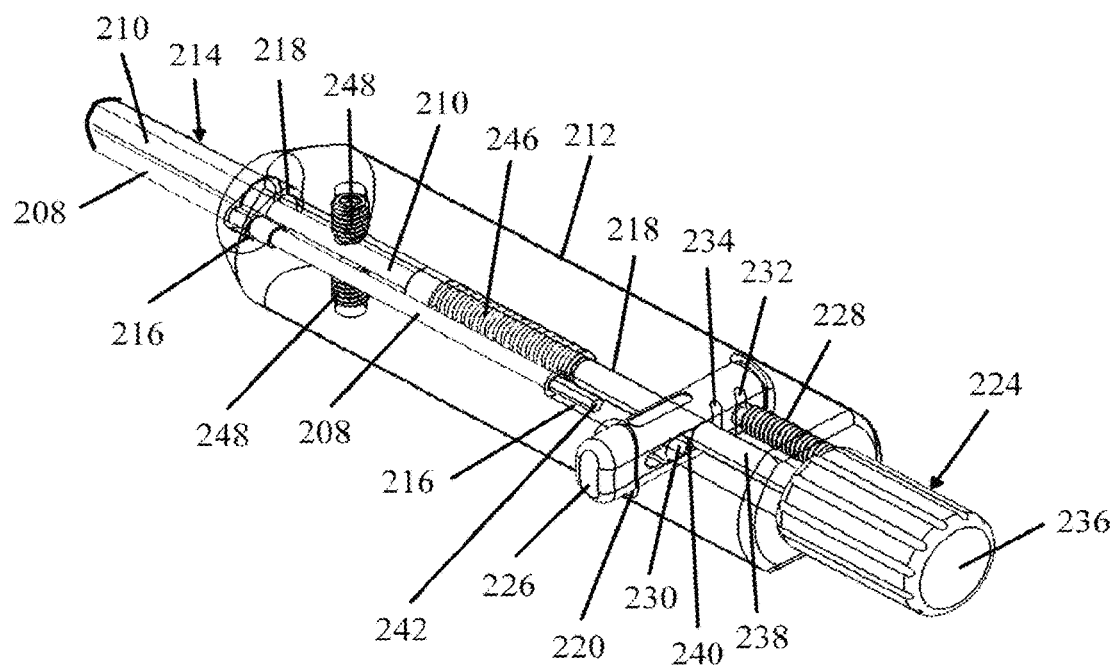
FIG. 16 is a truncated distal view of the handle end of the expansion tool of FIG. 15, in accordance with an aspect of the present invention.
Figure 17:
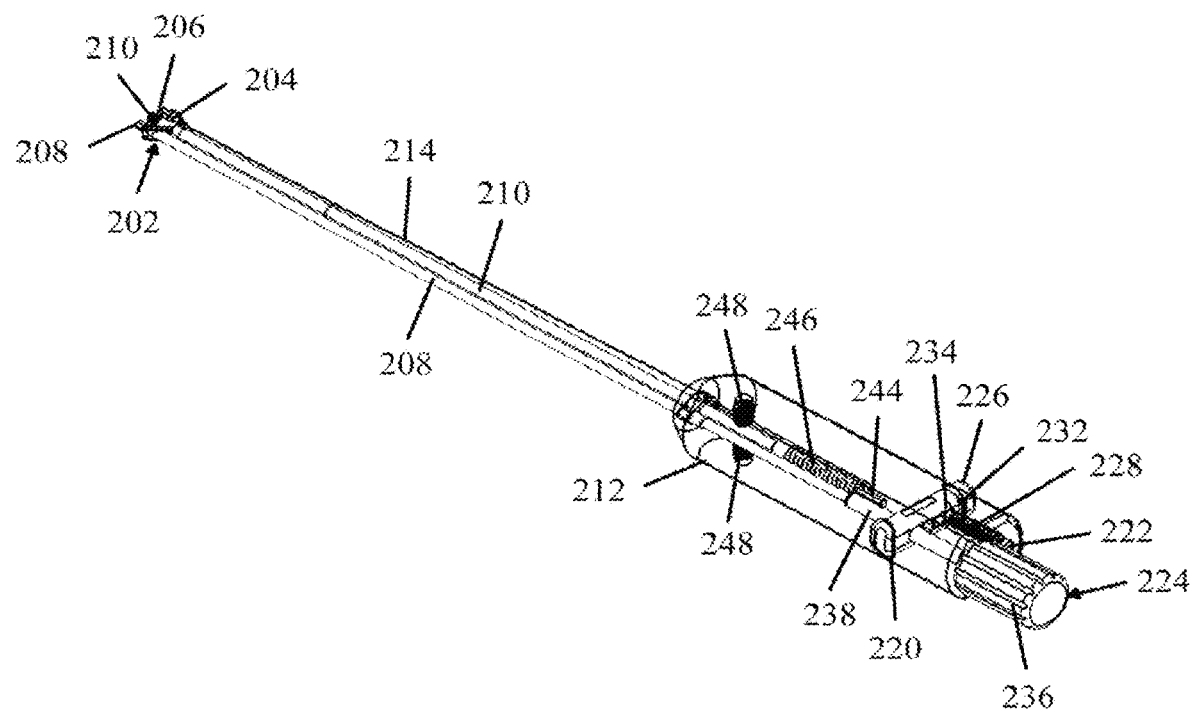
FIG. 17 is a perspective view of the expansion tool of FIG. 13 with a transparent outer housing and the knob in a second position, in accordance with an aspect of the present invention.
Figure 18:
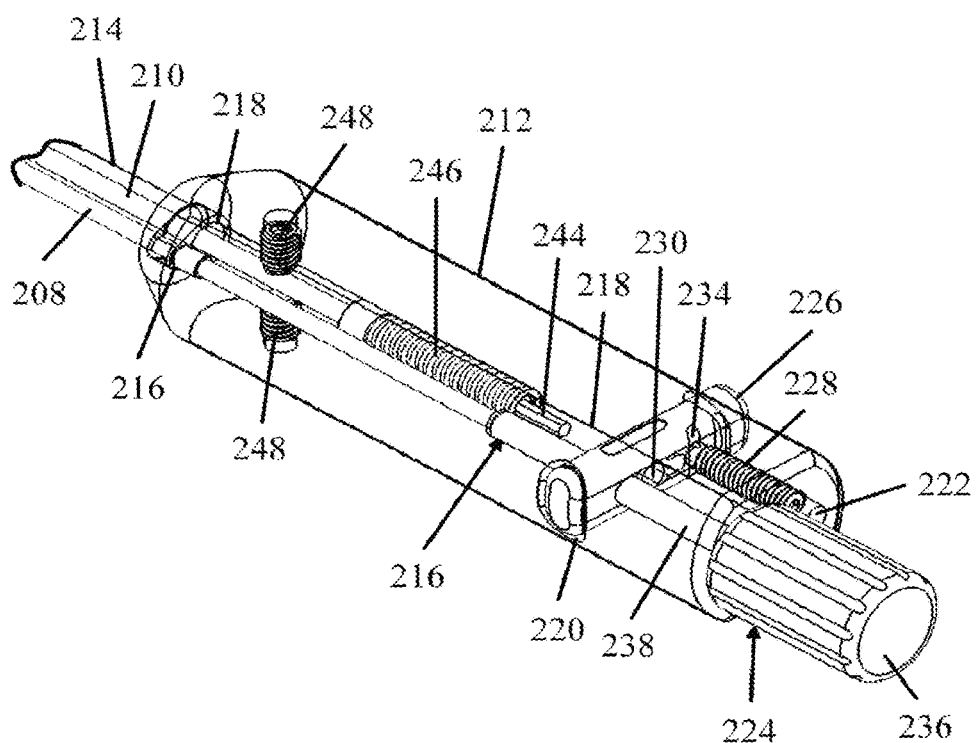
FIG. 18 is truncated distal view of the handle end of the expansion tool of FIG. 17, in accordance with an aspect of the present invention.

As seen in FIGS. 16 and 18, the adjustment mechanism 208 may pass into the first opening 216 from the distal end of the handle 212 enabling engagement with the distal end of the shaft 238 of the knob 224 when inserted into the first opening 216 from the proximal end of the handle 212. A tool engagement end 242 (see FIGS. 15-16) of the adjustment mechanism 208 couples with the distal end of the shaft 238 to enable rotation of the adjustment mechanism 208. The securement mechanism 210 may pass into the second opening 218 from the distal end of the handle 212 enabling engagement with the distal end of the shaft 238 of the knob 224 when inserted into the second opening 218 from the proximal end of the handle 212. In addition, the securement mechanism 210 may include a spring mechanism 246 inserted over the proximal end of the securement mechanism 210 to spring load the securement mechanism 210. A tool engagement end 244 of the securement mechanism 210 couples with the distal end of the shaft 238 to enable rotation of the securement mechanism 210. The tool engagement ends 242, 244 may have, for example, a hex male head, square, or other multi-lobed configuration to enable rotation of the adjustment mechanism 208 or securement mechanism 210, respectively. The shaft 238 of the knob 224 when inserted into either the first or second openings 216, 218 passes through a hole 230 in the actuation bar 226 before engaging the adjustment mechanism 208 or securement mechanism 210, respectively. The channel 240 in the shaft 238 of the knob 224 engages the hole 230 in the actuation bar 226 to lock the knob 224 in the first or second opening 216, 218.

Figure 19:
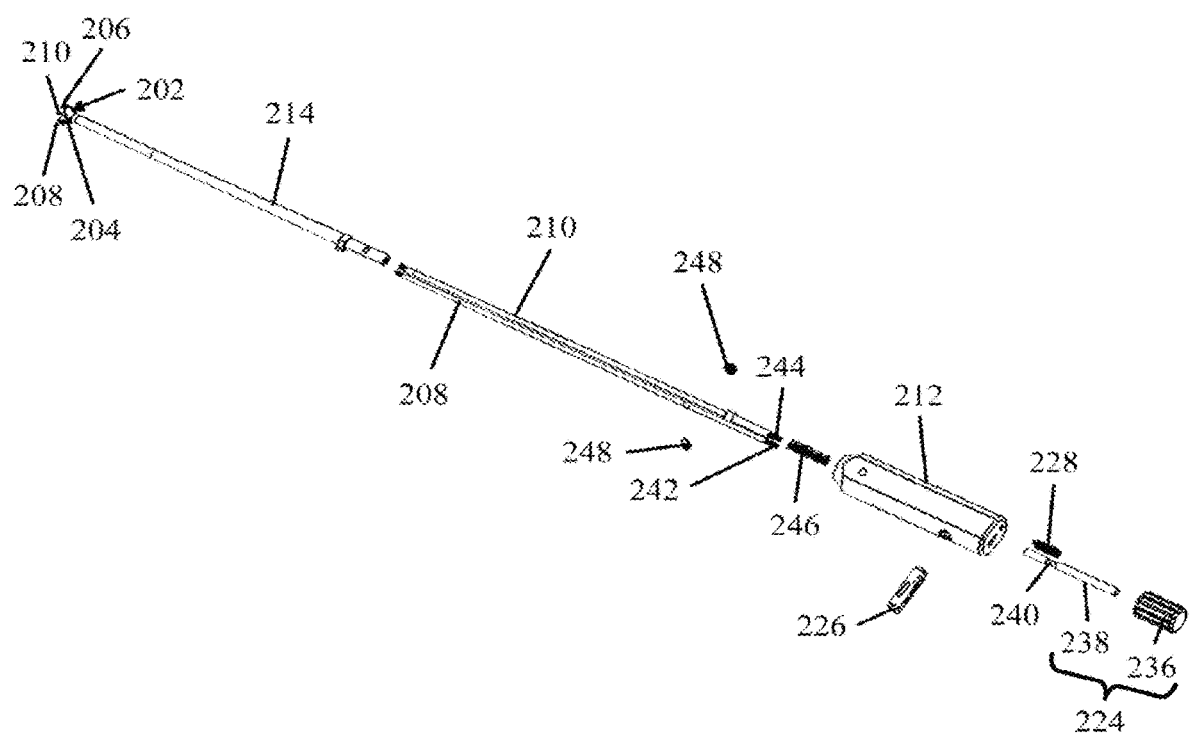
FIG. 19 is an exploded view of the tool of FIG. 13, in accordance with an aspect of the present invention.

During use a surgeon may insert the tool 200 into the implant 100 by aligning the protrusion 206 of the insertion end 202 of the tool 200 with the alignment channel 112 of the implant 100. Once the tool 200 and implant 100 are aligned and the actuation bar 226 is in an unlocked position the shaft 238 of the knob 224 may be inserted into the second opening 218 and coupled to the tool engagement end 244 of the securement mechanism 210. After the shaft 238 has coupled to the tool engagement end 244 of the securement mechanism 210, the actuation bar 226 may be moved to the first locked position, as shown in FIGS. 12, 15 and 16, and the actuation bar 226 engages the channel 240 in the shaft 238 of the knob 224, as shown in FIGS. 15, 16 and 19. As the actuation bar 226 is moved to lock the knob 224 into the second opening 218, the spring plunger 228 in the fourth opening 222 may engage a first channel 232 of the actuation bar 226 to lock the knob 224 in place in the handle 212. The head 236 of the knob 224 of the tool 200 may then be rotated which in turn will rotate the securement mechanism 210. As the knob 224 rotates the securement mechanism 210, the distal end of the securement mechanism 210 engages the threads 108 of the attachment opening 114 of the implant 100. The securement mechanism 210 of the tool will couple with the attachment opening 114 of the implant 100 to secure the implant 100 to the tool 200 for insertion into a patient. In addition, as the securement mechanism 210 engages the attachment opening 114 of the implant 100, the adjustment mechanism 208 of the tool will engage the opening 186 in the drive rod 180 of the implant 100.

Once the implant 100 is secured to the tool 200, the physician may remove the knob 224 from the second opening 218 of the handle 212 by moving the actuation bar 226 to the unlocked position. As the actuation bar 226 is moved from the first locked position, shown in FIGS. 12, 15 and 16, to the unlocked position the spring plunger 228 disengages the first channel 232. With the actuation bar 226 in an unlocked position the shaft 238 of the knob 224 may be inserted into the proximal end of the first opening 216 in the handle 212 to engage the tool engagement end 242 of the adjustment mechanism 208. Once the shaft 238 has coupled to the tool engagement end 242 of the adjustment mechanism 208, the actuation bar 226 may be moved to the second locked position, shown in FIGS. 17 and 18. As the actuation bar 226 is moved to the second locked position, the spring plunger 228 may engage a second channel 234 of the actuation bar 226 to lock the knob 224 into the first opening 216 in the handle 212. After the actuation bar 226 of the handle 212 is in the second locked position, the implant 100 may then be inserted into the desired position in the patient. The physician may then rotate the head 236 of the knob 224 which in turn will rotate the distal end of the adjustment mechanism 208. As the head 236 of the knob 224 is rotated, the adjustment mechanism 208, which is coupled to the opening 186 in the drive rod 180, engages the expansion mechanism 140 and expands the far end of the implant 100 to angle the top member 130 relative to the base member 110. The cogs or teeth 178 of the worm gear 184 on the end of the drive rod 180 are sized to mate with the corresponding serial depressions 152 of the gear 150 to facilitate rotation of the gear 150 when the knob 224 of the tool 200 is turned. Once the desired expansion of the implant 100 is achieved, the tool 200 may then be removed from the patient.

In the alternative embodiment shown in FIGS. 9-11, prior to removing the tool 200, the locking mechanism 192 may be inserted into the implant 100 to secure the top member 130 of the implant 100 in the desired expansion and/or retraction relative to the base member 110. The locking mechanism 192 may be inserted into the opening 186 in the drive rod 180 by first securing the insertion tool 200 or a similar tool to the opening 199 of the locking mechanism 192. As the locking mechanism 192 is inserted into the base member 110 and the drive rod 180, the shaft 194 of the locking mechanism 192 fits securely within the opening 186 of the drive rod 180. In addition, the plurality of protrusions 198 on the head 196 may engage the lip 129 in the adjustment opening 116 of the base member 110. In addition, the drive rod 180 may be recessed within the base member 110 to provide a cavity for insertion of the locking mechanism 192 into the base member 110, such that when the locking mechanism 192 is inserted into the base member 110 of the implant 100 it is flush with the exterior surface of the base member 110.

The tool 200 may be removed from the patient by removing the knob 224 from the first opening 216 of the handle 212. The knob 224 may be removed from the first opening 216 by moving the actuation bar 226 to the unlocked position to disengage the actuation bar 226 from the knob channel 240 and the spring plunger 228 from the first channel 232 in the actuation bar 226. Once the actuation bar 226 is in an unlocked position the shaft 238 of the knob 224 may be removed from the first opening 216 and inserted into the second opening 218 to engage the securement mechanism 210. After inserting the shaft 238 of the knob 224 in the second opening 218, the actuation bar 226 may be moved to the first locked position, as shown in FIGS. 15 and 16 to secure the knob shaft 238 in the second opening 218 of the handle 212. In the first locked position, the spring plunger 228 may again engage the first channel 232 to secure the knob 224 in the handle 212. The head 236 of the knob 224 may then be rotated to remove the distal end of the securement mechanism 210 from the attachment opening 114. As the securement mechanism 210 rotates it disengages the threads 108 of the attachment opening 114 and the protrusion 206 and adjustment mechanism 208 of the insertion end 202 of the tool 200 slide out of the alignment channel 112 and adjustment opening 116, respectively. It is also contemplated that the above method for inserting the implant 100 using tool 200 may be performed in alternative orders.

Figure 20:
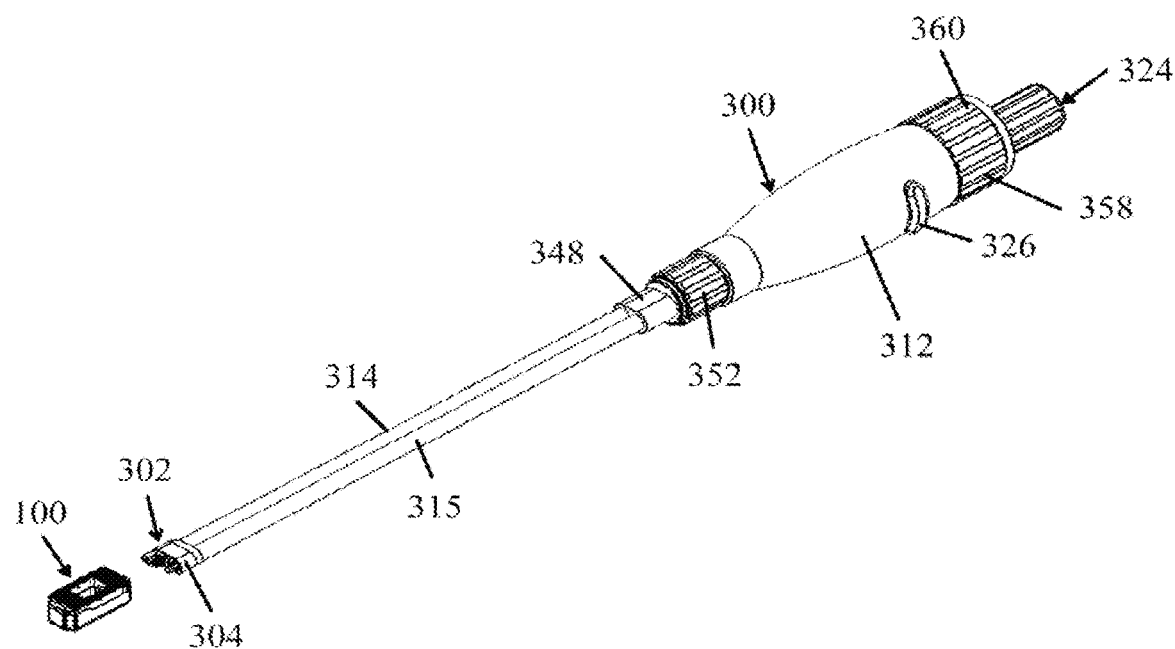
FIG. 20 is a perspective view of the expandable interbody fusion device of FIG. 1 and another embodiment tool, in accordance with an aspect of the present invention.

Referring now to FIGS. 20-28, an alternative embodiment tool 300 for inserting the implant 100 into a patient is shown. The tool 300 and the implant 100 may form an interbody fusion device system as shown in FIG. 20. The tool 300 is designed to engage the expansion mechanism 140 (see FIG. 8). The insertion end 302 of the tool 300 may be configured with a housing 304 including a protrusion 306 shaped to correspond to the alignment channel 112 in the base member 110. The insertion end 302 may also include an opening 308 for adjustment mechanism 342 or locking mechanism inserter 344 and a securement mechanism 310 which protrude out of the distal end of the housing 304. The adjustment mechanism 342 may be configured, for example, to have a hex male head, square, or other multi-lobed configuration that will allow for the user to rotate the knob 324 of the tool 300 and cause the expansion mechanism 140 to rotate. Opposite the insertion end 302, the tool 300 has a handle 312 which may be connected to the housing 304 of the insertion end 302 by a tube 314. The tube 314 may be coupled to the housing 304 on the distal end and secured to the handle 312 at the proximal end. The tube 314 may house the securement mechanism 310 which may extend from the handle 312 to the housing 304 inside the tube 314. In addition, a second tube 315 may extend between the housing 304 at the insertion end 302 and the handle 312, relatively parallel to and outside the tube 314, to house the adjustment mechanism 342 or locking mechanism inserter 344.

Figure 21:
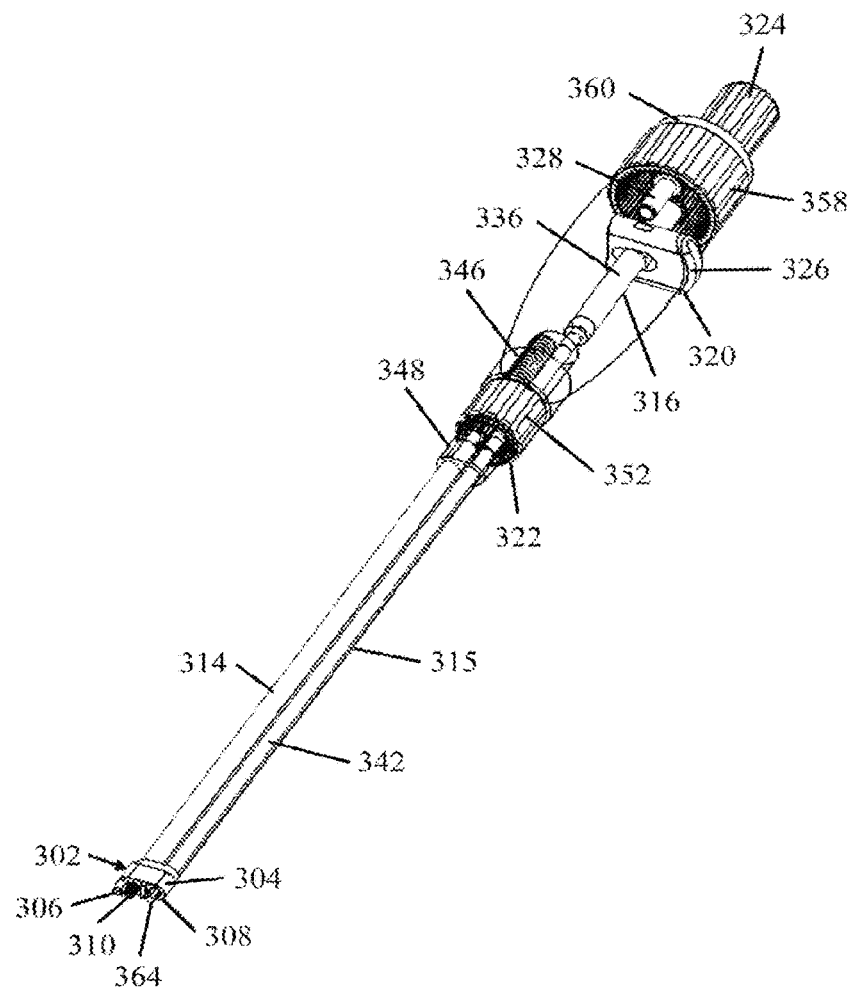
FIG. 21 is a perspective view of the tool of FIG. 20 with a transparent outer housing and intermediate housing, in accordance with an aspect of the present invention.
Figure 22:
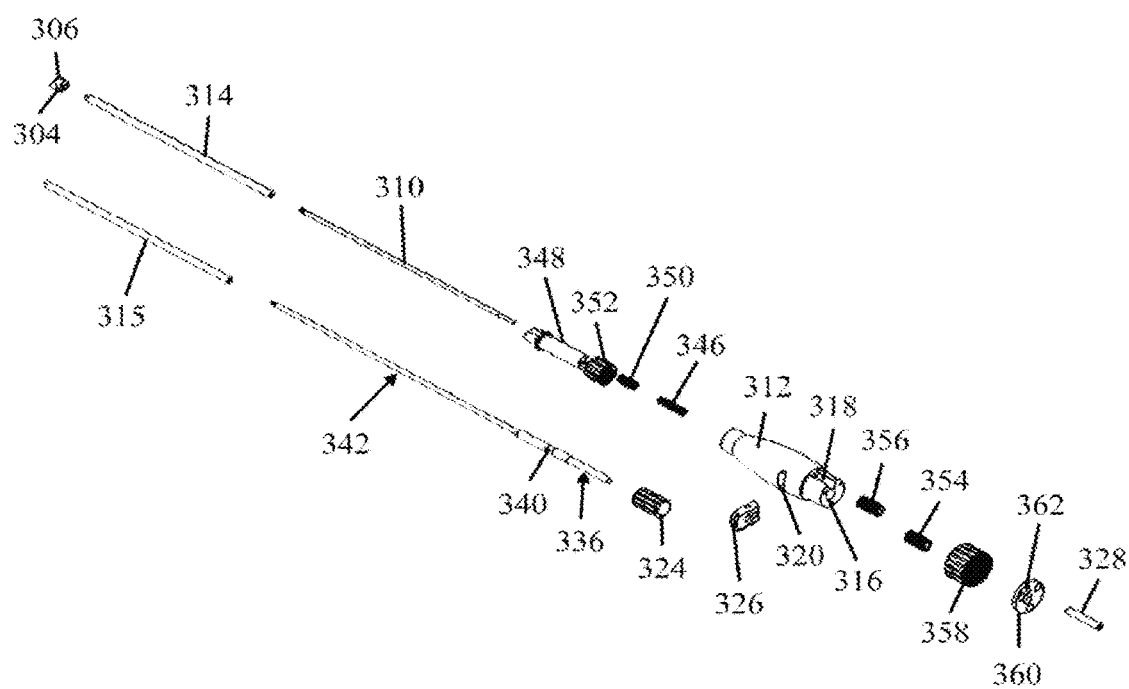
FIG. 22 is an exploded view of the tool of FIG. 20, in accordance with an aspect of the present invention.
Figure 23:
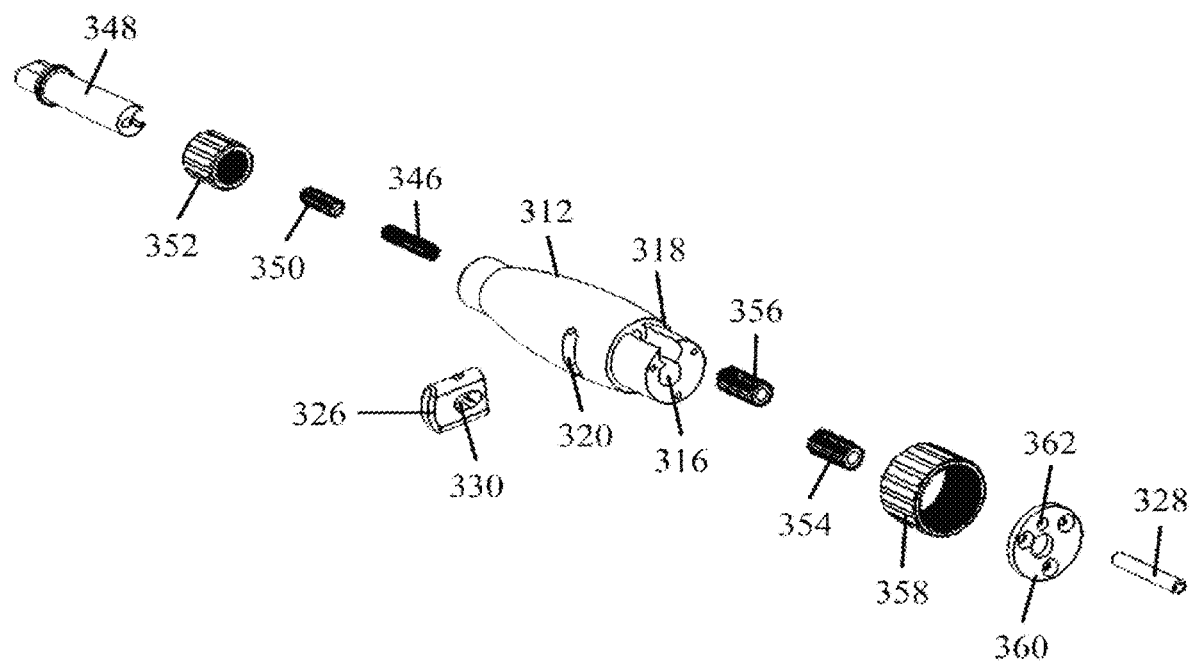
FIG. 23 is an exploded view of the handle portion of the tool of FIG. 20, in accordance with an aspect of the present invention.

As seen in FIGS. 21-23, the handle 312 of the tool 300 may also include a first opening 316 along the longitudinal axis of the handle 312. The handle 312 may also include a second opening 318 which may extend into the handle 312 from the proximal end of the handle 312 and run parallel with the first opening 316. In addition, the handle 312 of tool 300 may include a third opening 320 extending perpendicular to and engaging the first opening 316. The handle 312 may also include a knob 324 for attachment to a shaft 336, 338 of the adjustment mechanism 342 or locking mechanism inserter 344, respectively, which may be inserted into the first opening 316 at a proximal end of the handle 312, a gear shaft 328 for insertion into the second opening 318, and an actuation bar 326 for insertion into the third opening 320. The knob 324 may be attached to a shaft 336, 338 of the adjustment mechanism 342 or locking mechanism 344, respectively, and the shaft 336, 338 may extend out away from the inferior surface of the knob 324 when inserted. The shafts 336, 338 of the adjustment mechanism 342 or locking mechanism inserter 344 may also include a channel 340 for mating with the actuation bar 326 to secure the adjustment mechanism 342 or locking mechanism inserter 344 in the opening 316. The shafts 336, 338 of the adjustment mechanism 342 or locking mechanism inserter 344 when inserted into the first openings 316 pass through a hole 330 in the actuation bar 326. The channel 340 in the shafts 336, 338 of the adjustment mechanism 342 or locking mechanism inserter 344 engage the hole 330 in the actuation bar 326 to lock the adjustment mechanism 342 or locking mechanism inserter 344 in the first opening 316. The handle 312 may further include a fourth opening 322 in the distal end of the handle 312. The fourth opening 322 may allow the adjustment mechanism 342 or locking mechanism inserter 344 to pass out of the insertion end 302 of the tool 300. In addition, the fourth opening 322 may allow for the securement mechanism 310 to be attached to the distal end of the handle 312.

As shown in FIGS. 21-23, the handle 312 may also include an intermediate housing 348 that mates with the fourth opening 322 to secure the securement mechanism to the handle 312. A spring mechanism 346 may be inserted into the fourth opening 322 of the handle 312 to hold a first gear 350 inside of a second knob 352. The first gear 350 mates with the end of the securement mechanism 310 to enable rotation of the securement mechanism 310 by rotating the second knob 352 which in turn rotates the first gear 350 and the coupled securement mechanism 310. The rotation of the second knob 352 allows a physician to rotate the engagement end of the securement mechanism 310 to attach the implant 100 to the tool 300.

The proximal end of the handle 312 may also include a second gear 354 that sits in the first opening 316 and a third gear 356 that sits in the second opening 318, as shown in FIGS. 22 and 23. The first opening 318 may engage the second opening 318 to enable the gear teeth on the second and third gears 354, 356 to overlap such that rotation of the second gear 354 causes rotation of the third gear 356 and alternatively, such that rotation of the third gear 356 causes rotation of the second gear 354. The second opening 318 may also include a longitudinal opening enabling the gear teeth of the second gear 356 to engage the interior surface of the third knob 358, which engages the proximal end of the handle 312. The handle 312 may further include an end member 360 for mating with the third knob 358. The end member 360 may be secured to the third knob 358 using fasteners, not shown, such as screws. A gear shaft 328 may be inserted into handle 312 through an opening 362 in the end member 360 to engage a passage through the third gear 356.

Figure 24:
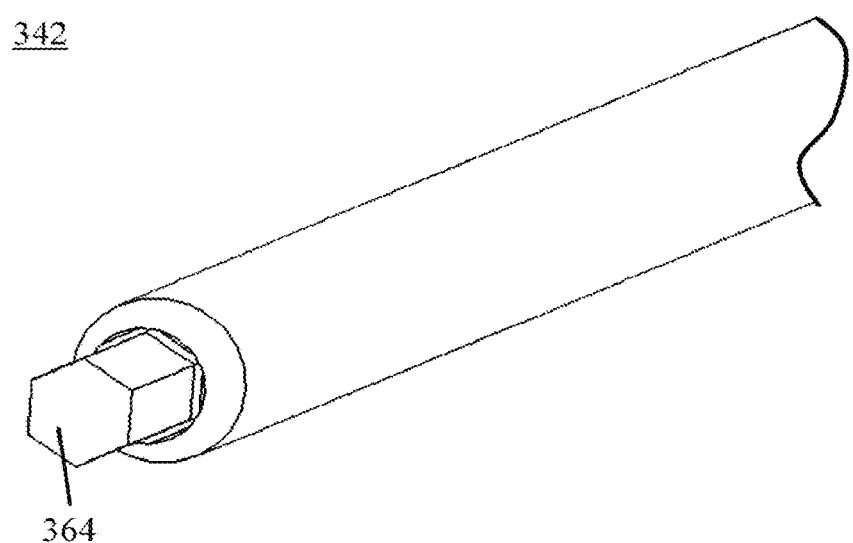
FIG. 24 is a truncated view of the adjustment end of the adjustment mechanism of the tool of FIG. 20, in accordance with an aspect of the present invention.
Figure 25:
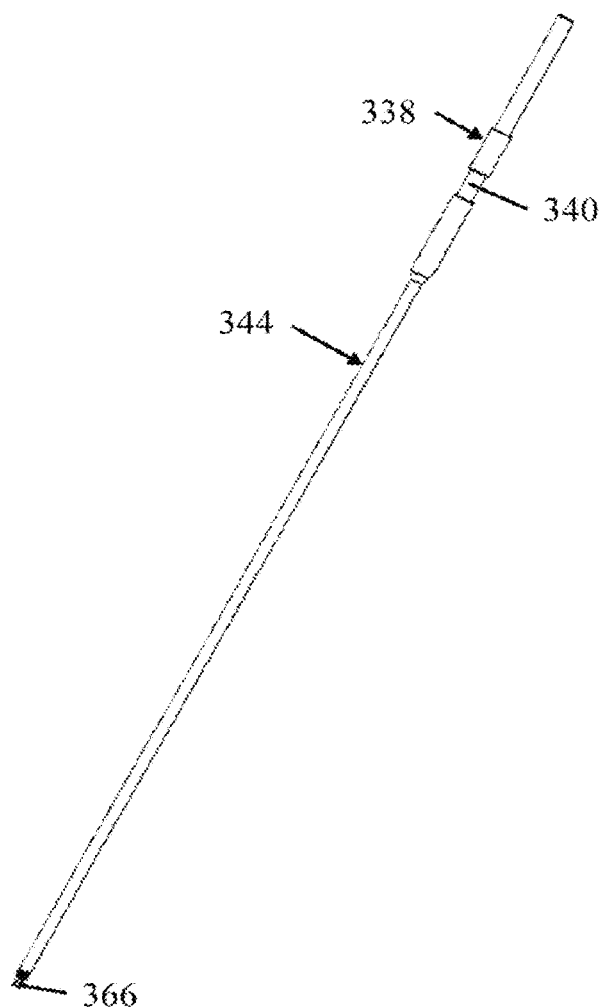
FIG. 25 is a perspective view of the locking mechanism inserter of the tool of FIG. 20, in accordance with an aspect of the present invention.
Figure 26:
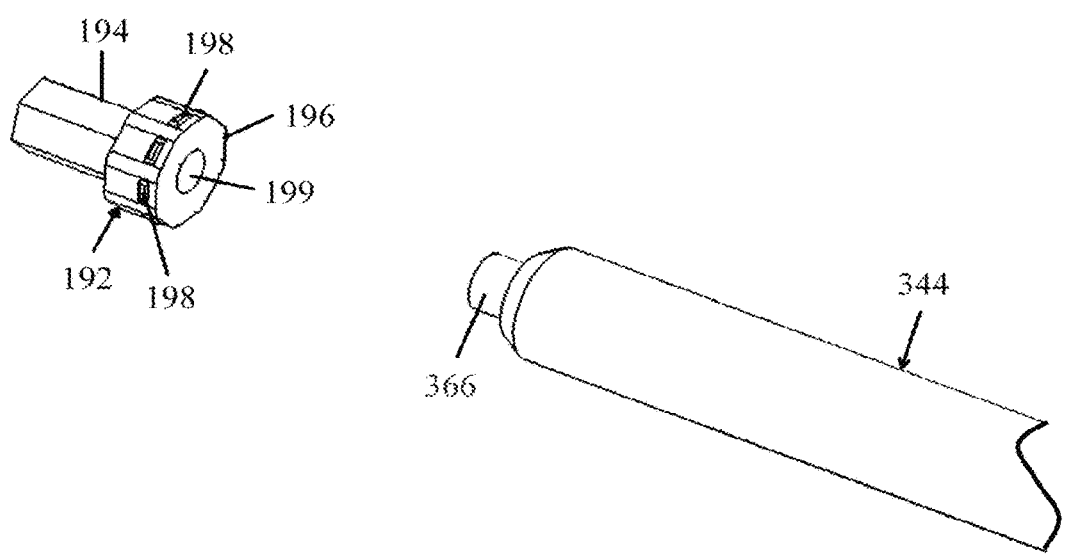
FIG. 26 is a truncated view of the locking mechanism inserter of the tool of FIG. 20 and the locking mechanism of FIG. 11, in accordance with an aspect of the present invention.

As seen in FIGS. 21-24, the adjustment mechanism 342 may pass into the first opening 316 from the proximal end of the handle 312, through the handle 312 and the second tube 315 and extend out of the opening 308 in the housing 304 enabling engagement with the implant 100. The proximal end of the adjustment mechanism 342 may extend through a passage in the second gear 354 and into the knob 324. The adjustment mechanism 342 may be coupled to the second gear 354 and the knob 324 enabling rotation of the proximal end of the adjustment mechanism 342 by the knob 324 and the third knob 358. The adjustment mechanism 352 may also pass through an intermediate housing 348 as it passes through the fourth opening 322 in the distal end of the handle 312 and into the second tube 315. When the adjustment mechanism 342 is in place within the tool 300, the adjustment end 364 extends out of the opening 308 in the housing 304 to enable engagement with the adjustment opening 116 in the implant 100. As shown in FIG. 24, the adjustment end 364 may have, for example, a hex male head, square, or other multi-lobed configuration to enable rotation of the drive rod 180 with a correspondingly shaped engagement end. Once the implant 100 is in a desired expansion or retraction, the physician may remove the adjustment mechanism 342 and insert the locking mechanism inserter 344 to lock the implant 100 in the desired expansion or retraction. The locking mechanism inserter 344, shown in FIGS. 25 and 26, may include an engagement end 366 with a shape corresponding to the opening 199 in the locking mechanism 192. The engagement end 366 of the tool 300 may be inserted into the opening 199 in the locking mechanism 192 for insertion of the locking mechanism 192 into the implant 100. During surgery, the locking mechanism inserter 344 with the locking mechanism 192 attached to the engagement end 366 will be inserted into tool 300 through the opening 316 in the handle 312, through the intermediate housing 348, through the second tube 315, and out of the opening 308 in the housing 304 of the tool 300 to engage the implant 100.

Figure 27:
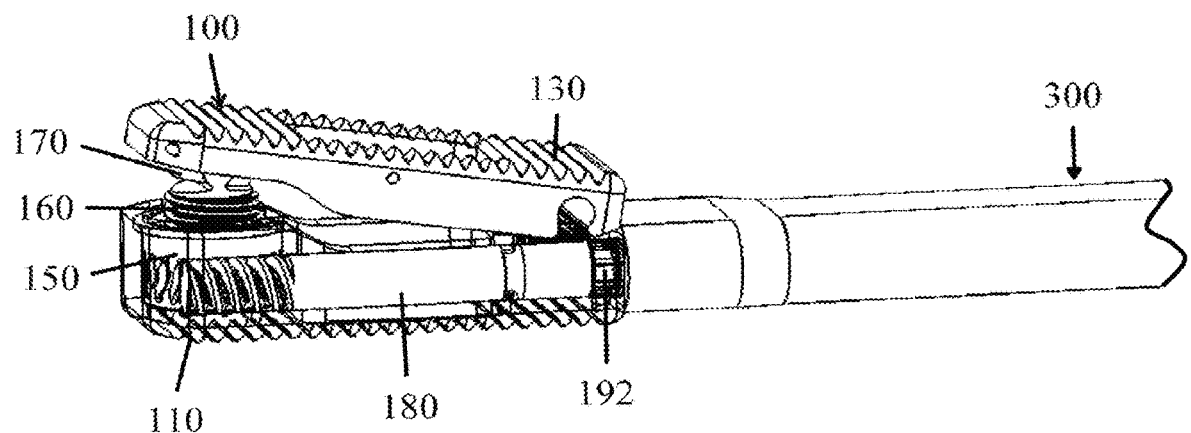
FIG. 27 is a truncated view of the tool of FIG. 20 with the locking mechanism inserter inserted into the implant of FIG. 1, in accordance with an aspect of the present invention.
Figure 28:
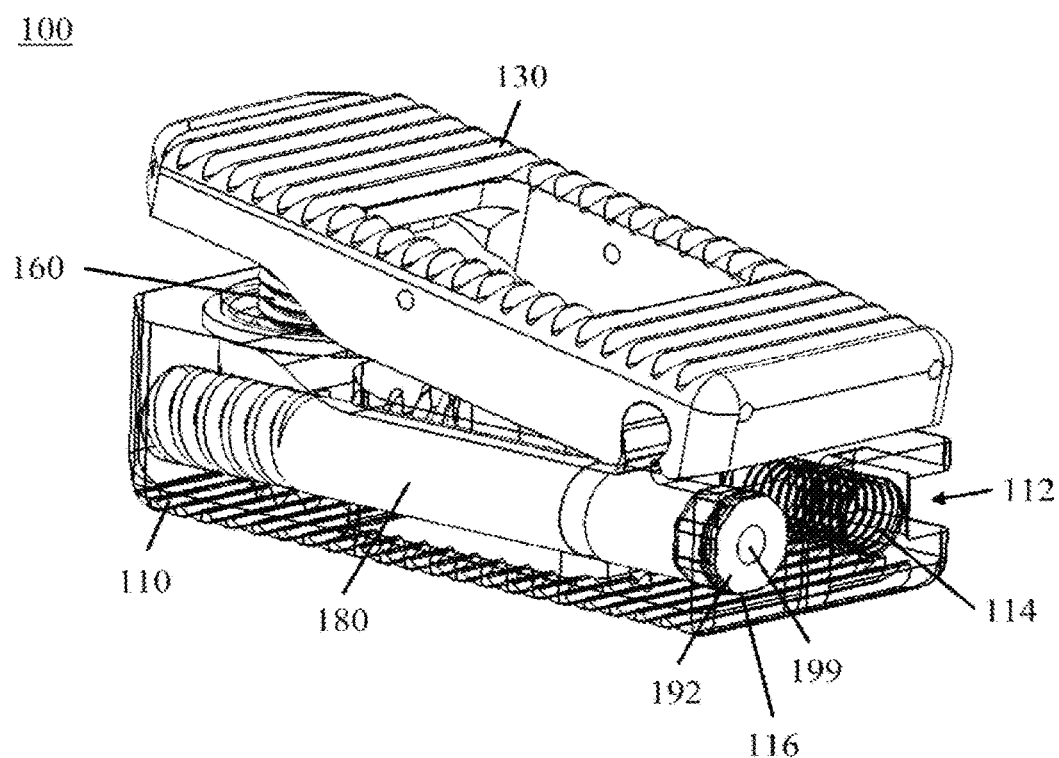
FIG. 28 is a perspective view of an implant with the locking mechanism of FIG. 11 inserted into the base member, in accordance with an aspect of the present invention.

As shown in FIGS. 27 and 28, the locking mechanism 192 may be inserted into the base member 110 and drive rod 180 using the locking mechanism inserter 344 (see FIG. 25-26) of the tool 300 to secure the implant 100 in the desired expansion or retraction. The drive rod 180 may be recessed within the adjustment opening 116 in the base member 110 of the implant 100 when the locking mechanism 192 is used. The tool 300 may be used in place of the tool 200 in the above surgical method to insert the implant 100 into a patient. If tool 300 was used in the above described method, the method may also include the steps of removing the adjustment mechanism 342 after expansion or retraction and inserting the locking mechanism inserter 344 to lock the implant 100 in the desired expansion or retraction using the locking mechanism 192.

Figure 34:
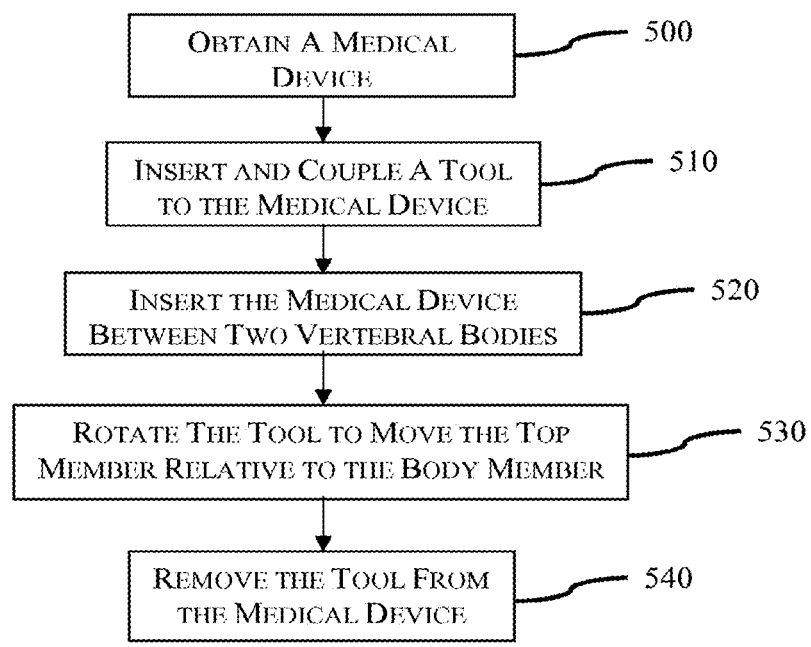
FIG. 34 depicts an embodiment of a surgical method for maintaining a space between two vertebral bodies in a spine.

As shown in FIG. 34 and described in greater detail above, the method may include obtaining a medical device 500, inserting and coupling a tool to the medical device 510, slidingly inserting the medical device into a space between two vertebral bodies 520, rotating a knob of the tool to move a first end of a top member in a vertical direction relative to a body member 530, and removing the tool from the medical device 540.

Figure 29:
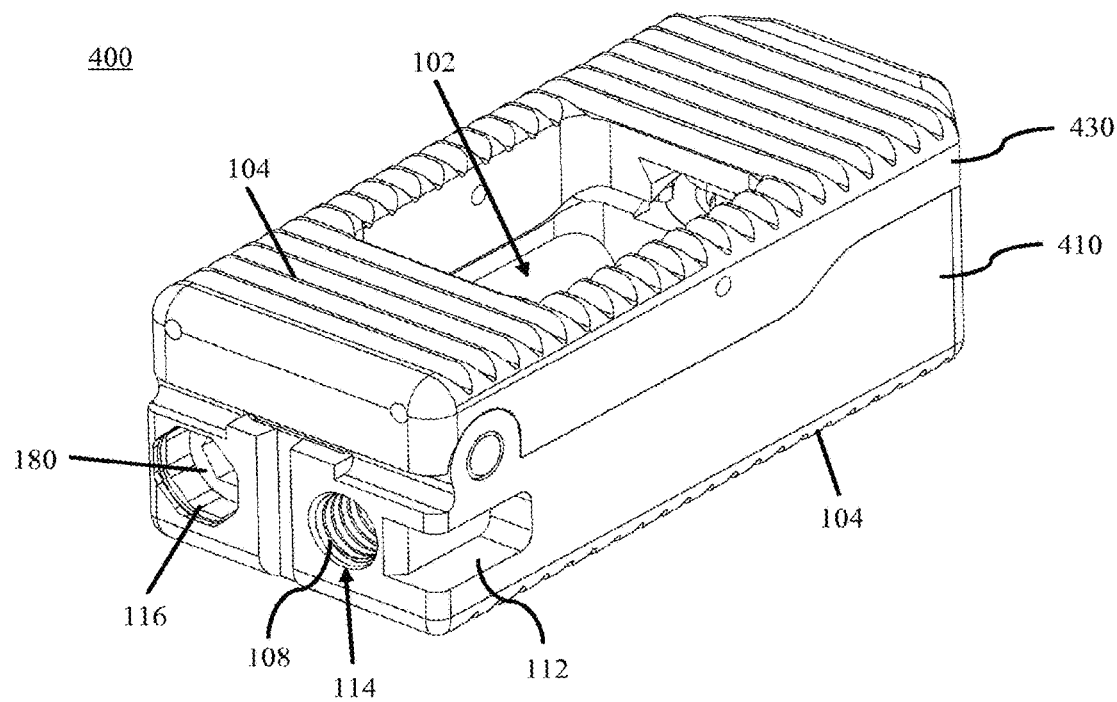
FIG. 29 is a posterior perspective view of another embodiment of an expandable interbody fusion device, in accordance with an aspect of the present invention.
Figure 30:
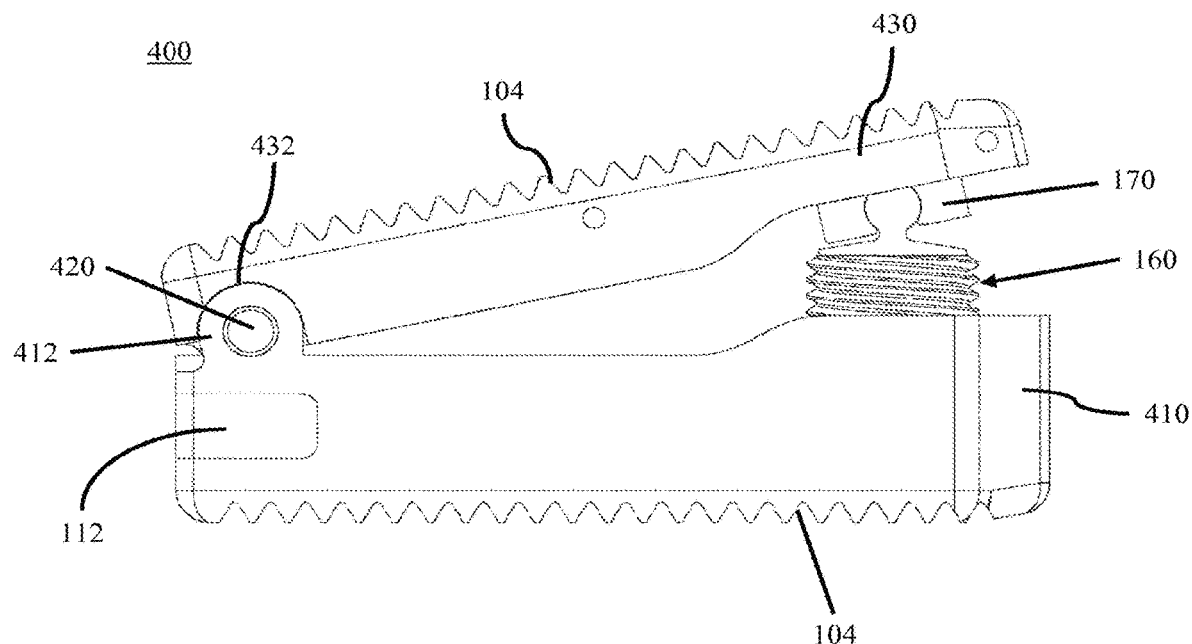
FIG. 30 is a side view of the expandable interbody fusion device of FIG. 29 with a moveable member extended, in accordance with an aspect of the present invention.

Another adjustable interbody fusion device 400 is shown in FIGS. 29-33. The device 400, as seen in FIGS. 29-30, may include at least one moveable top or superior member 430 and a base or bottom member 410. The top member 430 may be detachably coupled to the base member 410. The base member 410 and top member 430 may have at least one through hole or central opening 102. The base member 410 may include a bone contacting surface 104 and the top member 430 may also include a bone contacting surface 104. The at least one through hole or central opening 102 and the bone contacting surface 104 may be of the types described in greater detail above with reference to device 100.

Figure 31:
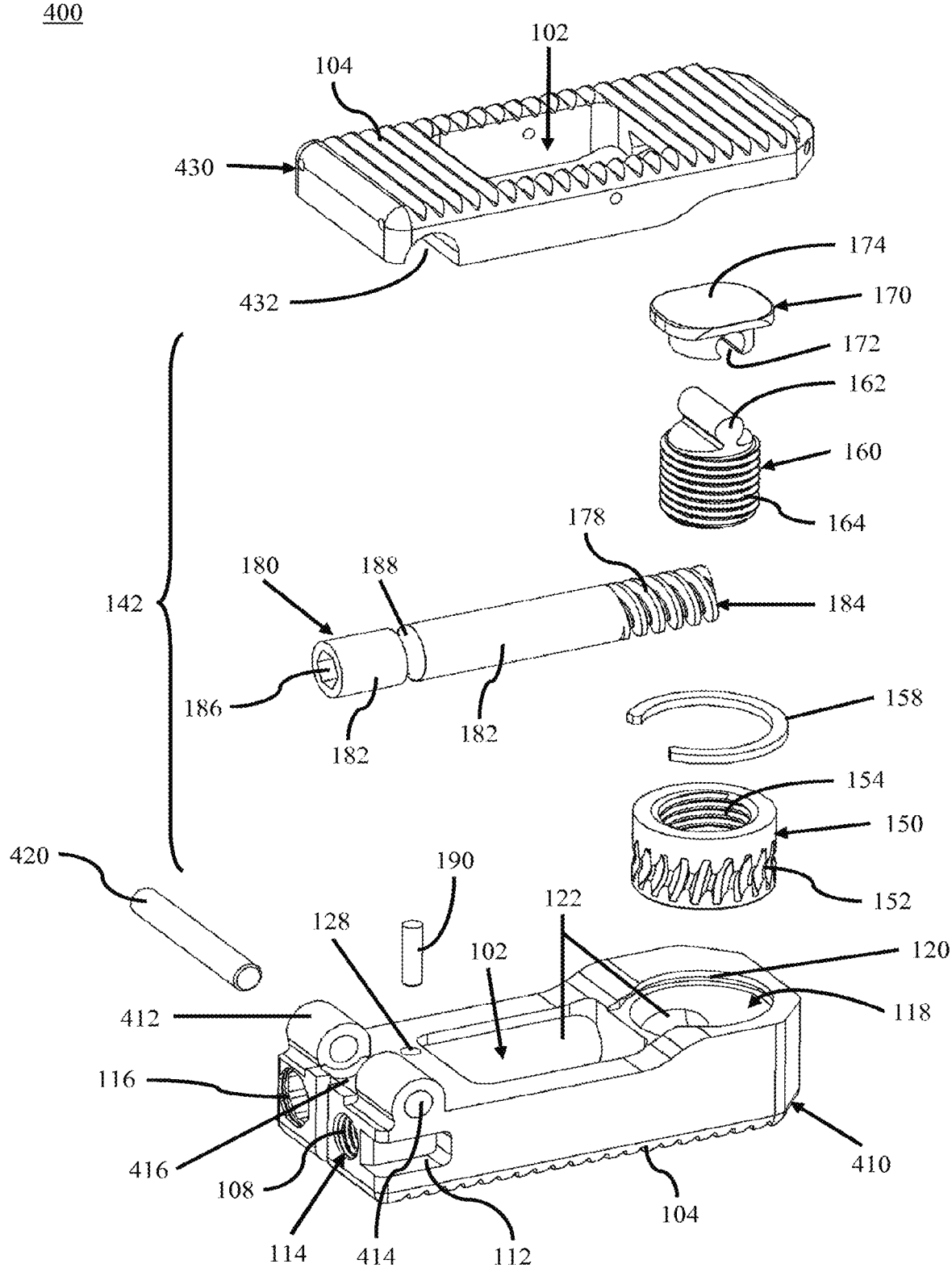
FIG. 31 is an exploded view of the expandable interbody fusion device of FIG. 29, in accordance with an aspect of the present invention.
Figure 32:
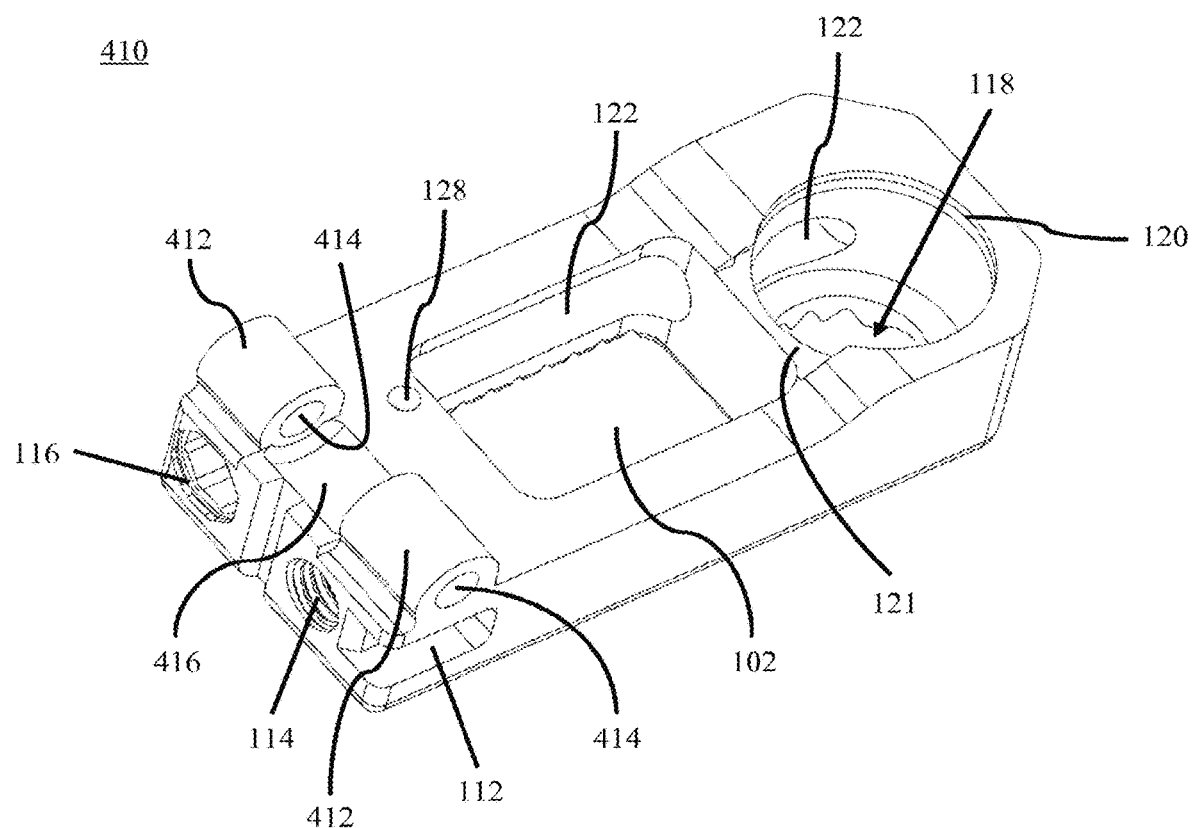
FIG. 32 is a superior perspective view of the expandable interbody fusion device of FIG. 29, in accordance with an aspect of the present invention.

As shown in FIGS. 29, 31 and 32, the base member 410 may include a tool alignment channel 112, a tool attachment opening 114, and an adjustment opening 116, as described above in greater detail with reference to device 100. The base member 410 may also include a hole or lumen 118 configured to receive the expansion mechanism 140 (see FIG. 8), as described in greater detail above with reference to device 100. The base member 410 may further include an internal circumferential shoulder 120, a notch 121, a channel 122, and an opening 128, as described in greater detail above with reference to device 100. The base member 410 may also include at least two pivot cylinders 412 each with at least one opening 414 and at least one hinge channel 416.

Figure 33:
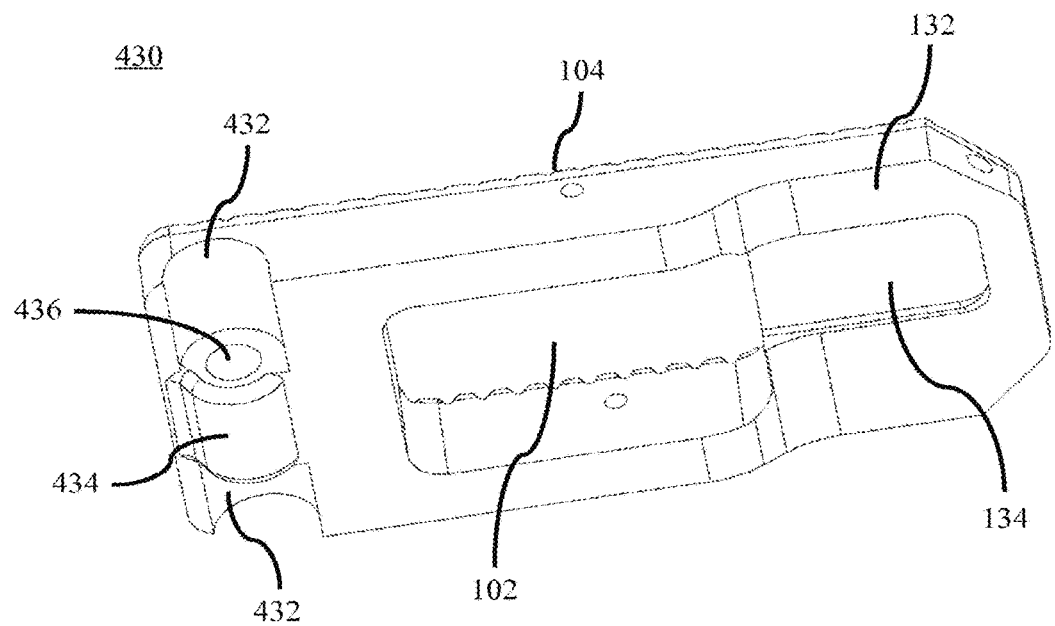
FIG. 33 is an inferior perspective view of the expandable interbody fusion device of FIG. 29, in accordance with an aspect of the present invention.

The top or superior member 430 is shown in greater detail in FIG. 33 and may include an undersurface 132 with a relief area 134 as described above in greater detail with respect to device 100. The top member 430 may also include at least two hinge channels 432 and at least one pivot cylinder 434 with at least one opening 436. The at least two hinge channels 432 of the top member 430 may be configured to mate with the at least two pivot cylinders 412 of the base member 410 (see FIG. 32). Likewise, the at least one pivot cylinder 434 may be configured to mate with the at least one hinge channel 416 of the base member 410 (see FIG. 32). The openings 414, 436 are configured to align and receive a pin 420 when the top member 430 is placed on the base member 410 to enable the implant 400 to pivot on one end such that the implant 400 extends on a first end while remaining closed on a second end. The pivot cylinders 412, 434, hinge channels 416, 432, and pin 420 allow the top member 430 to pivot or rotate around the outer diameters of the pivot cylinders 412, 434 when the expansion assembly 142 (see FIG. 8) is extended or retracted causing the top member 430 to tilt or slant relative to the base member 410.

An exploded view of the implant 400 is shown in FIG. 31. The implant 400 includes the expansion mechanism 140 as shown in FIG. 8. As described in greater detail above with reference to device 100, the expansion mechanism 140 may include an expansion assembly 142 and a drive rod 180. The expansion assembly 142 may include the cylindrical gear 150, the support means 158, the threaded rod 160, and the load head 170 as described above with reference to device 100.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

Although the example embodiments have been depicted and described in detail herein, it will be apparent to those skilled in the relevant art that various modifications, additions and substitutions can be made without departing from its essence and therefore these are to be considered to be within the scope of the following claims.

What is claimed:

1. An interbody fusion device, the device comprising:
   a first body member comprising a first end, a second end, a first bone contacting surface, a first inner surface opposite the first bone contacting surface, and at least one projection extending from the first inner surface along a first end portion of the first body member forming a pivot cylinder;
   a second body member comprising a first end, a second end, a second bone contacting surface, and a second inner surface opposite the second bone contacting surface including a pivot channel extending along a first end portion of the second body member, wherein the pivot cylinder is configured to engage the pivot channel to enable the pivot channel to pivot on, and about a longitudinal axis of, the pivot cylinder; and
   a movement mechanism for moving the second body member relative to the first body member causing the second body member to angularly pivot relative to the first body member on, and about the longitudinal axis of, the pivot cylinder such that an angle between the first and second bone contacting surfaces is varied,
   wherein the position and orientation of the pivot cylinder are fixed with respect to the first inner surface of the first body member, and
   wherein the position and orientation of the pivot channel are fixed with respect to the second inner surface of the second body member.

2. The interbody fusion device of claim 1, wherein the pivot cylinder has an outer surface sized to correspond to an inner surface of the pivot channel to enable the pivot channel to rotate on and relative to the pivot cylinder to thereby enable the second body member to rotate on and relative to the first body member.

3. The interbody fusion device of claim 1, wherein the at least one projection forming the pivot cylinder and the inner surface of the first body member are integral.

4. The interbody fusion device of claim 1, wherein the first body member further comprises:
   a tool alignment channel on the first end;
   a tool attachment opening on the first end adjacent to the tool alignment channel; and
   an adjustment opening on the first end adjacent to the tool attachment opening.

5. The interbody fusion device of claim 1, wherein the longitudinal axis of the pivot cylinder extends along a width of the first body member defined by opposite lateral sides of the first body member extending between the first and second ends thereof.

6. An interbody fusion device, the device comprising:
   a first body member comprising a first end, a second end, a first bone contacting surface, a first inner surface opposite the first bone contacting surface, and at least one projection extending from the first inner surface along a first end portion of the first body member forming a pivot cylinder;
   a second body member comprising a first end, a second end, a second bone contacting surface, and a second inner surface opposite the second bone contacting surface including a pivot channel extending along a first end portion of the second body member, wherein the pivot cylinder is configured to engage the pivot channel to enable the pivot channel to pivot on and about the pivot cylinder; and
   a movement mechanism for moving the second body member relative to the first body member causing the second body member to pivot relative to the first body member on and about the pivot cylinder,
   wherein the pivot cylinder is in a fixed positional relationship with respect to the first inner surface of the first body member, and
   wherein the first body member further comprises:
      a tool alignment channel on the first end;
      a tool attachment opening on the first end adjacent to the tool alignment channel; and
      an adjustment opening on the first end adjacent to the tool attachment opening.

7. The interbody fusion device of claim 6, wherein the first body member further comprises:
   a hole near the second end of the first body member and extending from the first bone contacting surface to the first inner surface, the hole configured to receive at least a portion of the movement mechanism; and
   a channel extending from the adjustment opening at the first end along a lateral side of the first body member to engage the hole.

8. The interbody fusion device of claim 7, wherein the second body member further comprises a relief area positioned on the second inner surface at the second end and aligned with the hole.

9. The interbody fusion device of claim 8, wherein the movement mechanism comprises:
   an expansion assembly configured to be placed in the hole of the first body member and engage the relief area of the second body member; and
   a drive rod configured for insertion into the channel of the first body member to engage the expansion assembly.

10. The interbody fusion device of claim 9, wherein the expansion assembly comprises:
    a cylindrical gear configured to nest in the hole;
    a support means positioned adjacent to the cylindrical gear;
    a threaded rod comprising:
       a pivot cylinder on a first end; and
       a plurality of external threads extending along the length of the threaded rod; and
    a load head with a top surface and a bottom surface comprising:
       a head surface on the top surface and configured to engage the relief area of the second body member; and
       a distal channel on the bottom surface and configured to engage the pivot cylinder of the threaded rod.

11. The interbody fusion device of claim 10, wherein the drive rod comprises:
    a cylindrical shaft with a first end and a second end;
    a worm gear at the first end;
    an opening at the second end; and
    a channel in the cylindrical shaft positioned between the first end and the second end.

12. The interbody fusion device of claim 11, wherein the hole of the first body member further comprises:
    an internal circumferential shoulder configured to receive the support means of the expansion assembly; and
    a notch engaging the hole and the internal circumferential shoulder.

13. The interbody fusion device of claim 11, further comprising:
    a pin configured for insertion into the first body member to engage the channel in the cylindrical shaft of the drive rod.

14. The interbody fusion device of claim 11, further comprising:
a locking mechanism configured to engage the adjustment opening in the first body member and the opening in the drive rod, the locking mechanism comprising:
a head including an opening for engaging an insertion tool and a plurality of protrusions configured to engage the adjustment opening; and
a shaft extending away from the head and configured to engage the opening in the drive rod.

15. The interbody fusion device of claim 6, wherein the position and orientation of the pivot channel are fixed with respect to the second inner surface of the second body member, and wherein the movement mechanism causes the second body member to pivot relative to the first body member on and about the pivot cylinder such that an angle between the first and second bone contacting surfaces is varied.

16. The interbody fusion device of claim 6, wherein the pivot cylinder defines a longitudinal axis, and wherein the longitudinal axis of the pivot cylinder extends along a width of the first body member defined by opposite lateral sides of the first body member extending between the first and second ends thereof.

17. An interbody fusion device system, comprising:
an interbody fusion device, comprising:
a base member comprising a first end, a second end, a first bone contacting surface, a first inner surface opposite the first bone contacting surface, and at least one projection extending from the first inner surface along a first end portion of the base member forming a pivot cylinder, wherein the pivot cylinder is fixed to the first inner surface;
a top member comprising a first end, a second end, a second bone contacting surface, and a second inner surface opposite the second bone contacting surface including a hinge channel extending along a first end portion of the top member, wherein the pivot cylinder is configured to engage the hinge channel to enable the hinge channel to pivot on and about the pivot cylinder; and
an expansion mechanism for moving the top member relative to the base member to cause the top member to pivot relative to the base member on and about the pivot cylinder; and
an insertion tool, comprising:
a handle;
an insertion end;
at least one tube extending away from the handle and connecting the handle and the insertion end;
a first knob configured to couple to the handle; and
an actuation bar moveable between a first position and a second position to enable the first knob to engage an adjustment mechanism in the first position and a securement mechanism in the second position.

18. The interbody fusion device system of claim 17, wherein the base member further comprises:
a tool alignment channel on the first end;
a tool attachment opening on the first end; and
an adjustment opening on the first end.

19. The interbody fusion device system of claim 18, wherein the insertion end of the insertion tool comprises:
a housing with an alignment protrusion configured to engage the tool alignment channel;
the adjustment mechanism which extends from the handle to the insertion end and out of the housing to engage the adjustment opening; and
the securement mechanism which extends from the handle to the insertion end and out of the housing to engage the tool attachment opening.

20. The interbody fusion device system of claim 18, wherein the insertion end of the insertion tool comprises:
a housing with an alignment protrusion configured to engage the tool alignment channel of the base member;
a locking mechanism inserter which extends from the handle to the insertion end and out of the housing to engage a locking mechanism for insertion into the expansion mechanism; and
the securement mechanism which extends from the handle to the insertion end and out of the housing to engage the tool attachment opening.

21. A method for assembling an interbody fusion device, comprising:
obtaining a first member, an expansion mechanism, and a second member, wherein the first member includes a pivot cylinder fixed to a first end portion of an inner surface thereof, and wherein the second member includes a hinge channel positioned on an inner surface thereof along a length of a first end thereof;
inserting the expansion mechanism into the first member;
securing a first portion of the expansion mechanism in the first member;
coupling the first member to the second member including inserting the pivot cylinder into the hinge channel to enable the second member to angularly pivot relative to the first member about a longitudinal axis of the pivot cylinder such that an angle between bone contacting surfaces of the first and second members is varied; and
aligning the second member with the first member and a second portion of the expansion mechanism,
wherein the position and orientation of the pivot cylinder are fixed with respect to the inner surface of the first member, and
wherein the position and orientation of the hinge channel are fixed with respect to the inner surface of the second member.

22. The method of claim 21, wherein the first member comprises:
an adjustment opening on a first end thereof;
a hole near a second end thereof and extending from the inner surface to an inferior surface, the hole comprising:
an internal circumferential shoulder; and
a notch engageable with the hole and the internal circumferential shoulder; and
a channel extending from the adjustment opening along a lateral side of the bottom first member to the hole,
wherein the expansion mechanism comprises:
an expansion assembly comprising:
a cylindrical gear;
a support means;
a threaded rod configured to engage the cylindrical gear; and
a load head configured to couple to the threaded rod and bear against the second member; and
a drive rod comprising:
a cylindrical shaft with a first end and a second end;
a worm gear at the first end;
an opening at the second end; and
a channel in the cylindrical shaft positioned between the first end and the second end; and
wherein the second member comprises:
a relief area positioned on a second end portion of the inner surface.

23. The method of claim 22, wherein inserting the expansion mechanism into the first member comprises:
aligning the cylindrical gear in the hole of the first member;
inserting the support means into the internal circumferential shoulder adjacent to the cylindrical gear;
coupling the load head to the threaded rod;
inserting the threaded rod with the coupled load head into the cylindrical gear by aligning external threads of the threaded rod with internal threads of the cylindrical gear;
sliding the drive rod into the channel of the first member to engage the cylindrical gear; and
coupling the pivot cylinder and hinge channel to align the first member and second member.

24. The interbody fusion device of claim 21, wherein the pivot cylinder defines a longitudinal axis, and wherein the longitudinal axis of the pivot cylinder extends along a width of the first member defined by opposite lateral sides of the first member extending between the first end portion and a second end portion thereof.

25. An interbody fusion device, the device comprising:
a first body member comprising a first end, a second end, a first bone contacting surface, a first inner surface opposite the first bone contacting surface, and at least one projection extending from the first inner surface along a first end portion of the first body member forming a pivot cylinder;
a second body member comprising a first end, a second end, a second bone contacting surface, and a second inner surface opposite the second bone contacting surface including a pivot channel extending along a first end portion of the second body member, wherein the pivot cylinder is configured to engage the pivot channel to enable the pivot channel to pivot on and about the pivot cylinder; and
a movement mechanism for moving the second body member relative to the first body member causing the second body member to pivot relative to the first body member on and about the pivot cylinder,
wherein the pivot cylinder is in a fixed positional relationship with respect to the first inner surface of the first body member, and
wherein the pivot cylinder defines a longitudinal axis, and wherein the longitudinal axis of the pivot cylinder extends along a width of the first body member defined by opposite lateral sides of the first body member extending between the first and second ends thereof.

26. The interbody fusion device of claim 25, wherein the first body member further comprises:
a tool alignment channel on the first end;
a tool attachment opening on the first end adjacent to the tool alignment channel; and
an adjustment opening on the first end adjacent to the tool attachment opening.

27. The interbody fusion device of claim 25, wherein the position and orientation of the pivot channel are fixed with respect to the second inner surface of the second body member, and wherein the movement mechanism causes the second body member to pivot relative to the first body member on and about the pivot cylinder such that an angle between the first and second bone contacting surfaces is varied.

* * * * *

UNITED STATES PATENT AND TRADEMARK OFFICE
CERTIFICATE OF CORRECTION

PATENT NO. : 10,667,925 B2
APPLICATION NO. : 15/985301
DATED : June 2, 2020
INVENTOR(S) : Emerick et al.

Page 1 of 1

It is certified that error appears in the above-identified patent and that said Letters Patent is hereby corrected as shown below:

In the Claims

Column 18, Line 50: Claim 22, Delete "lateral side of the bottom first member" and insert -- lateral side of the first member --

Signed and Sealed this
Twenty-first Day of July, 2020

Andrei Iancu
*Director of the United States Patent and Trademark Office*